(12) United States Patent
Beardsley et al.

(10) Patent No.: US 7,950,562 B2
(45) Date of Patent: May 31, 2011

(54) SURGICAL INSTRUMENT WITH REPLACEABLE LOADING UNIT

(75) Inventors: John W. Beardsley, Wallingford, CT (US); Paul A. Scirica, Huntington, CT (US)

(73) Assignee: Tyco Healthcare Group LP, North Haven, CT (US)

(*) Notice: Subject to any disclaimer, the term of this patent is extended or adjusted under 35 U.S.C. 154(b) by 4 days.

(21) Appl. No.: 11/701,116

(22) Filed: Jan. 31, 2007

(65) Prior Publication Data
US 2008/0179374 A1    Jul. 31, 2008

(51) Int. Cl.
*A61B 17/068* (2006.01)
*B25G 3/16* (2006.01)

(52) U.S. Cl. .............. 227/176.1; 227/19; 227/175.1; 403/348; 403/349

(58) Field of Classification Search ............. 227/175.1, 227/176.1, 19; 403/348, 349, 324, 325
See application file for complete search history.

(56) References Cited

U.S. PATENT DOCUMENTS

| | | | |
|---|---|---|---|
| 5,104,025 A * | 4/1992 | Main et al. ................. | 227/175.1 |
| 5,258,010 A | 11/1993 | Green et al. | |
| 5,307,976 A | 5/1994 | Olson et al. | |
| 5,318,221 A | 6/1994 | Green et al. | |
| 5,348,259 A * | 9/1994 | Blanco et al. ............. | 248/276.1 |
| 5,381,943 A | 1/1995 | Allen et al. | |
| 5,397,324 A | 3/1995 | Carroll et al. | |
| 5,403,327 A | 4/1995 | Thornton et al. | |
| 5,413,268 A | 5/1995 | Green et al. | |
| 5,439,155 A * | 8/1995 | Viola ........................ | 227/176.1 |
| 5,443,197 A | 8/1995 | Malis et al. | |
| 5,452,836 A * | 9/1995 | Huitema et al. ........... | 227/176.1 |
| 5,452,837 A | 9/1995 | Williamson, IV et al. | |
| 5,462,215 A * | 10/1995 | Viola et al. ................ | 227/176.1 |
| 5,465,895 A | 11/1995 | Knodel et al. | |
| 5,485,947 A | 1/1996 | Olson et al. | |
| 5,487,500 A | 1/1996 | Knodel et al. | |
| 5,489,058 A | 2/1996 | Plyley et al. | |
| 5,529,235 A * | 6/1996 | Boiarski et al. ........... | 227/175.1 |
| 5,553,765 A | 9/1996 | Knodel et al. | |
| 5,562,241 A | 10/1996 | Knodel et al. | |
| 5,564,615 A * | 10/1996 | Bishop et al. ............. | 227/175.1 |
| 5,577,654 A | 11/1996 | Bishop | |
| 5,588,580 A | 12/1996 | Paul et al. | |
| 5,588,581 A | 12/1996 | Conlon et al. | |
| 5,597,107 A | 1/1997 | Knodel et al. | |
| 5,601,224 A | 2/1997 | Bishop et al. | |
| 5,605,272 A | 2/1997 | Witt et al. | |
| 5,626,587 A | 5/1997 | Bishop et al. | |

(Continued)

OTHER PUBLICATIONS

European Search Report for corresponding EP 08 25 0373, date of completion is Sep. 28, 2010 (3 pages).

*Primary Examiner* — Rinaldi I Rada
*Assistant Examiner* — Gloria R Weeks

(57) ABSTRACT

A surgical stapling device has an elongated body and a removable loading unit and a securing structure for securing the loading unit onto the elongated body. Guiding ramps guide the movement of the loading unit as it is mounted onto the elongated body. A movable yoke secures the loading unit onto the elongated body. A sensor mechanism is engaged by the loading unit and moves with the securing structure. The locking structure has a first position for blocking movement of the sensor mechanism and preventing removal of the loading unit. The locking unit has a second position for allowing the loading unit to be removed from the device.

16 Claims, 22 Drawing Sheets

U.S. PATENT DOCUMENTS

| | | |
|---|---|---|
| 5,632,432 A | 5/1997 | Schulze et al. |
| 5,634,584 A | 6/1997 | Okorocha et al. |
| 5,634,930 A | 6/1997 | Thornton et al. |
| 5,662,258 A | 9/1997 | Knodel et al. |
| 5,662,259 A | 9/1997 | Yoon |
| 5,662,662 A | 9/1997 | Bishop et al. |
| 5,665,085 A * | 9/1997 | Nardella .................. 606/41 |
| 5,673,840 A | 10/1997 | Schulze et al. |
| 5,680,982 A | 10/1997 | Schulze et al. |
| 5,692,668 A | 12/1997 | Schulze et al. |
| 5,697,542 A | 12/1997 | Knodel et al. |
| 5,704,534 A | 1/1998 | Huitema et al. |
| 5,752,644 A | 5/1998 | Bolanos et al. |
| 5,762,255 A | 6/1998 | Chrisman et al. |
| 5,762,256 A | 6/1998 | Mastri et al. |
| 5,766,153 A * | 6/1998 | Eggers et al. ............... 604/114 |
| 5,769,303 A | 6/1998 | Knodel et al. |
| 5,779,131 A | 7/1998 | Knodel et al. |
| 5,779,132 A | 7/1998 | Knodel et al. |
| 5,782,396 A | 7/1998 | Mastri et al. |
| 5,797,537 A | 8/1998 | Oberlin et al. |
| 5,797,538 A | 8/1998 | Heaton et al. |
| 5,820,009 A | 10/1998 | Melling et al. |
| 5,826,776 A | 10/1998 | Schulze et al. |
| 5,865,361 A | 2/1999 | Milliman et al. |
| 5,901,895 A | 5/1999 | Heaton et al. |
| 5,954,259 A | 9/1999 | Viola et al. |
| 6,010,054 A | 1/2000 | Johnson et al. |
| 6,032,849 A | 3/2000 | Mastri et al. |
| 6,079,606 A | 6/2000 | Milliman et al. |
| 6,109,500 A | 8/2000 | Alli et al. |
| 6,241,139 B1 | 6/2001 | Milliman et al. |
| 6,330,965 B1 | 12/2001 | Milliman et al. |
| 6,488,196 B1 | 12/2002 | Fenton, Jr. |
| 6,592,597 B2 | 7/2003 | Grant et al. |
| 6,602,252 B2 | 8/2003 | Mollenauer |
| 6,656,193 B2 | 12/2003 | Grant et al. |
| 6,669,073 B2 | 12/2003 | Milliman et al. |
| 6,722,552 B2 | 4/2004 | Fenton, Jr. |
| 6,755,338 B2 | 6/2004 | Hahnen et al. |
| 6,786,382 B1 | 9/2004 | Hoffman |
| 6,830,174 B2 | 12/2004 | Hillstead et al. |
| 6,905,057 B2 | 6/2005 | Swayze et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,059,508 B2 | 6/2006 | Shelton, IV et al. |
| 7,083,075 B2 | 8/2006 | Swayze et al. |
| 7,097,089 B2 | 8/2006 | Marczyk |
| 7,111,769 B2 | 9/2006 | Wales et al. |
| 7,287,682 B1 * | 10/2007 | Ezzat et al. ................. 227/175.1 |
| 7,354,447 B2 * | 4/2008 | Shelton et al. ................. 606/219 |
| 2001/0030219 A1 | 10/2001 | Green et al. |
| 2002/0117533 A1 | 8/2002 | Milliman et al. |
| 2003/0009192 A1 | 1/2003 | Corsaro |
| 2004/0108357 A1 | 6/2004 | Milliman et al. |
| 2004/0199181 A1 | 10/2004 | Knodel et al. |
| 2004/0232195 A1 | 11/2004 | Shelton, IV et al. |
| 2004/0232196 A1 | 11/2004 | Shelton, IV et al. |
| 2004/0232197 A1 | 11/2004 | Shelton, IV et al. |
| 2004/0232199 A1 | 11/2004 | Shelton, IV et al. |
| 2004/0232200 A1 | 11/2004 | Shelton, IV et al. |
| 2004/0232201 A1 | 11/2004 | Wenchell et al. |
| 2004/0243151 A1 | 12/2004 | Demmy et al. |
| 2005/0006429 A1 | 1/2005 | Wales et al. |
| 2005/0006430 A1 | 1/2005 | Wales |
| 2005/0006431 A1 | 1/2005 | Shelton, IV et al. |
| 2005/0006432 A1 | 1/2005 | Racenet et al. |
| 2005/0006434 A1 | 1/2005 | Wales et al. |
| 2005/0023324 A1 | 2/2005 | Doll et al. |
| 2005/0067457 A1 | 3/2005 | Shelton, IV et al. |
| 2005/0067458 A1 | 3/2005 | Swayze et al. |
| 2005/0067459 A1 | 3/2005 | Swayze et al. |
| 2005/0067460 A1 | 3/2005 | Milliman et al. |
| 2005/0103819 A1 | 5/2005 | Racenet et al. |
| 2005/0119669 A1 | 6/2005 | Demmy |
| 2005/0127131 A1 | 6/2005 | Mastri et al. |
| 2005/0173490 A1 | 8/2005 | Shelton, IV |
| 2005/0178813 A1 | 8/2005 | Swayze et al. |
| 2005/0184123 A1 | 8/2005 | Scirica |
| 2005/0184124 A1 | 8/2005 | Scirica et al. |
| 2005/0184125 A1 | 8/2005 | Marczyk |
| 2005/0216055 A1 | 9/2005 | Scirica et al. |
| 2005/0263562 A1 | 12/2005 | Shelton, IV et al. |
| 2005/0279804 A1 | 12/2005 | Scirica et al. |
| 2006/0016853 A1 | 1/2006 | Racenet |
| 2006/0022014 A1 | 2/2006 | Shelton, IV et al. |
| 2006/0022015 A1 | 2/2006 | Shelton, IV et al. |
| 2006/0043147 A1 | 3/2006 | Mastri et al. |
| 2006/0049229 A1 | 3/2006 | Milliman et al. |
| 2006/0060630 A1 | 3/2006 | Shelton, IV et al. |
| 2006/0097026 A1 | 5/2006 | Shelton, IV |
| 2006/0151567 A1 | 7/2006 | Roy |
| 2006/0175375 A1 | 8/2006 | Shelton, IV et al. |
| 2006/0180634 A1 | 8/2006 | Shelton, IV et al. |
| 2006/0201990 A1 | 9/2006 | Mastri et al. |
| 2006/0201991 A1 | 9/2006 | Mastri et al. |
| 2006/0226195 A1 | 10/2006 | Scirica et al. |

* cited by examiner

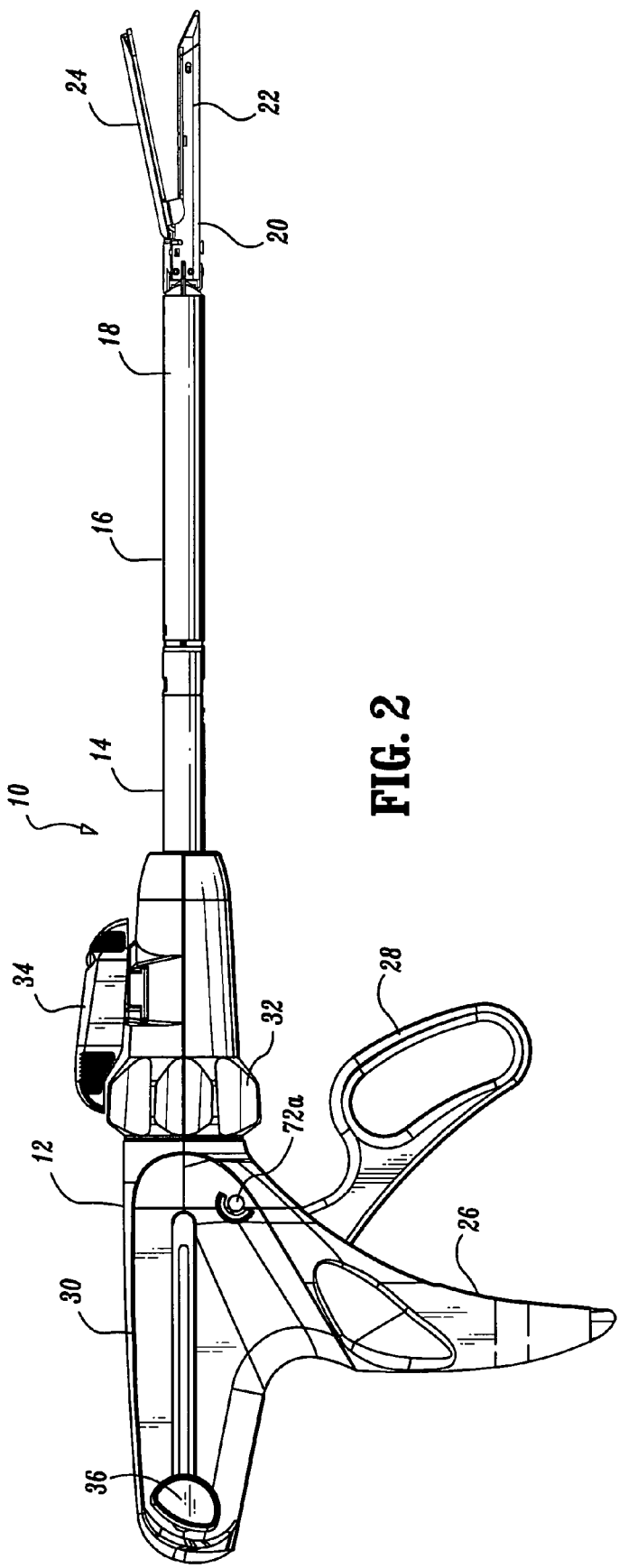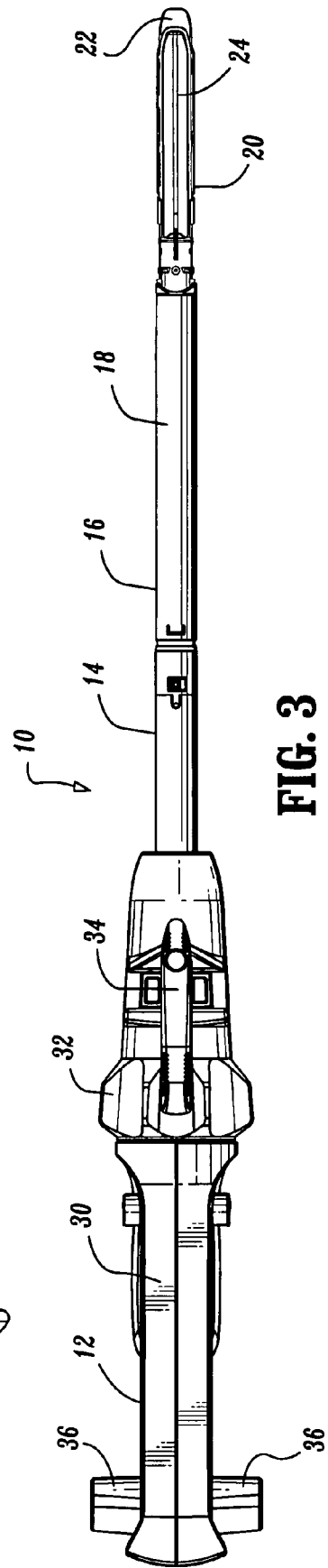
FIG. 2
FIG. 3

SURGICAL INSTRUMENT WITH REPLACEABLE LOADING UNIT

BACKGROUND

1. Technical Field

This application relates to a surgical stapling device for applying staples to tissue having a locking mechanism for securing a loading unit onto the surgical stapling device.

2. Background of Related Art

Surgical devices for applying surgical fasteners to tissue are well known. Endoscopic surgical devices for applying staples, clips or other fasteners include a handle assembly for actuating the device, an endoscopic shaft and a tool assembly at the distal end of the endoscopic shaft. Certain of these devices are designed for use with replaceable loading units housing the staples or fasteners. For example, in using an endoscopic linear stapler, the user may select a loading unit with staples of a selected size and arranged in one or more lines of staples having a selected staple line length. After firing, the user may remove the loading unit, select another loading unit of the same or different size, and fire staples from the instrument again. Endoscopic surgical staplers having four lines of staples, arranged in pairs on either side of a cut line, are known.

Loading units in the form of replaceable cartridges are known. In addition, loading units having a tool assembly, including a cartridge, anvil, drive assembly and knife are known. Such loading units have the benefit of providing a new knife with each loading of the loading unit.

Although interfaces between the surgical stapling device endoscopic shaft and the loading unit are known, improvements in the ease of loading and unloading of the loading unit are desired.

SUMMARY

In a first aspect of the present disclosure, a surgical instrument comprises a loading unit having a tool assembly, and an elongated body. The elongated body has a proximal end and a distal end. The distal end of the elongated body includes a securing structure for securing the loading unit onto the elongated body. The securing structure includes at least one guiding ramp and a moveable yoke with a first and a second position. The loading unit is secured on the elongated body when the yoke is in the second position. The at least one guiding ramp is arranged to guide movement of the loading unit in a predetermined direction toward engagement with the yoke, and the yoke is movable toward the second position as the loading unit is moved in the predetermined direction.

The loading unit has a projecting part for engaging the yoke and the at least one guiding ramp defines an arcuate path. The securing structure includes a ring defining a passage. Two guiding ramps are defined by the ring and extend in the passage.

The guiding ramps are helical in shape and are disposed approximately 180 degrees apart. Each of the at least one guiding ramp extends toward the proximal end of the elongated body.

The ring is attached to the distal end of the elongated body and the yoke is movably mounted to the ring so that the yoke is located proximally of the ring. The yoke is preferably rotatably mounted to the ring through an inter-engaging groove and ridge structure for allowing rotation.

The yoke has at least one protrusion for engagement by the projecting part on the loading unit. Preferably, the yoke has a pair of protrusions for being positioned on either side of the projecting part. The pair of protrusions is disposed adjacent a proximal end of the guiding ramp when the yoke is in the first position and defines a receiving space for the projecting part.

The securing structure has a ledge and the projecting part of the loading unit is proximal to the ledge when the yoke is in the second position so that the loading unit is secured onto the elongated body.

In a further aspect of the present disclosure, a surgical instrument comprises an elongated body having a proximal end, a distal end, and a rod extending therethrough, and a loading unit removably mountable with the distal end of the elongated body. The loading unit has a tool assembly. A sensor mechanism is arranged for engagement by the loading unit and for movement with the loading unit upon mounting the loading unit on the distal end of the elongated body. A handle assembly includes a locking structure having a first position for blocking movement of the sensor mechanism and a second position for allowing movement of the sensor mechanism so that the loading unit is removable from the elongated body when the sensor mechanism is in the second position.

The locking structure engages the rod when the locking structure is in the second position. This prevents movement of the rod when the loading unit is not mounted on the elongated body of the instrument. The locking structure has a plunger arranged to engage the rod. The rod has a notch arranged for engagement by the plunger. The locking structure includes a button that is accessible by the user of the surgical instrument and which can be used to change the locking structure from the first position to the second position.

The sensor mechanism preferably includes a sensor tube which is attached to a movable yoke at a distal end of the sensor tube. The movable yoke is arranged for engagement by and movement with the loading unit. The sensor tube is attached to a release flange at a proximal end thereof. The locking structure includes a tang for blocking movement of the release flange when the locking structure is in the first position. The release flange includes a cam surface for camming a plunger into engagement with the rod.

In another aspect of the present disclosure, a method of mounting a loading unit onto a surgical instrument comprises providing a surgical instrument with a handle assembly and an elongated body, the elongated body having a guiding ramp terminating at a receiving space defined by rotatable securing structure, and providing a loading unit with a tool assembly. The loading unit is engaged with the guiding ramp on the elongated body of the surgical instrument. The loading unit is rotated so that the loading unit follows the guiding ramp and engages the securing structure, and the loading unit is rotated into a secured position with respect to the elongated body so that the securing structure rotates with the loading unit. The securing structure is locked when the loading unit is in the secured position. Preferably, a structure is provided for releasing the securing structure.

In a further aspect, a method of removing a loading unit from a surgical instrument comprises providing a surgical instrument with a handle assembly and an elongated body, the elongated body defining movable securing structure, the handle assembly having a locking structure with a first position blocking movement of the securing structure and a second position allowing movement of the securing structure. A loading unit with a distal tool assembly and a proximal housing portion is provided. The loading unit is secured on the elongated body by the securing structure. The locking structure Is moved from the first position to the second position, and the loading unit is removed from the surgical instrument.

The loading unit is removed by rotating the loading unit, the loading unit interacting with the securing structure so that the securing structure moves with the loading unit. The loading unit is moved by rotating the loading unit and the securing structure rotates therewith.

BRIEF DESCRIPTION OF DRAWINGS

Various preferred embodiments of the presently disclosed surgical stapling device are described herein with reference to the drawings, in which:

FIG. 2 is a side elevation view of the surgical stapling device of FIG. 1;

FIG. 3 is a top plan view of the surgical stapling device of FIGS. 1-2;

DETAILED DESCRIPTION OF EMBODIMENTS

Figure 1:
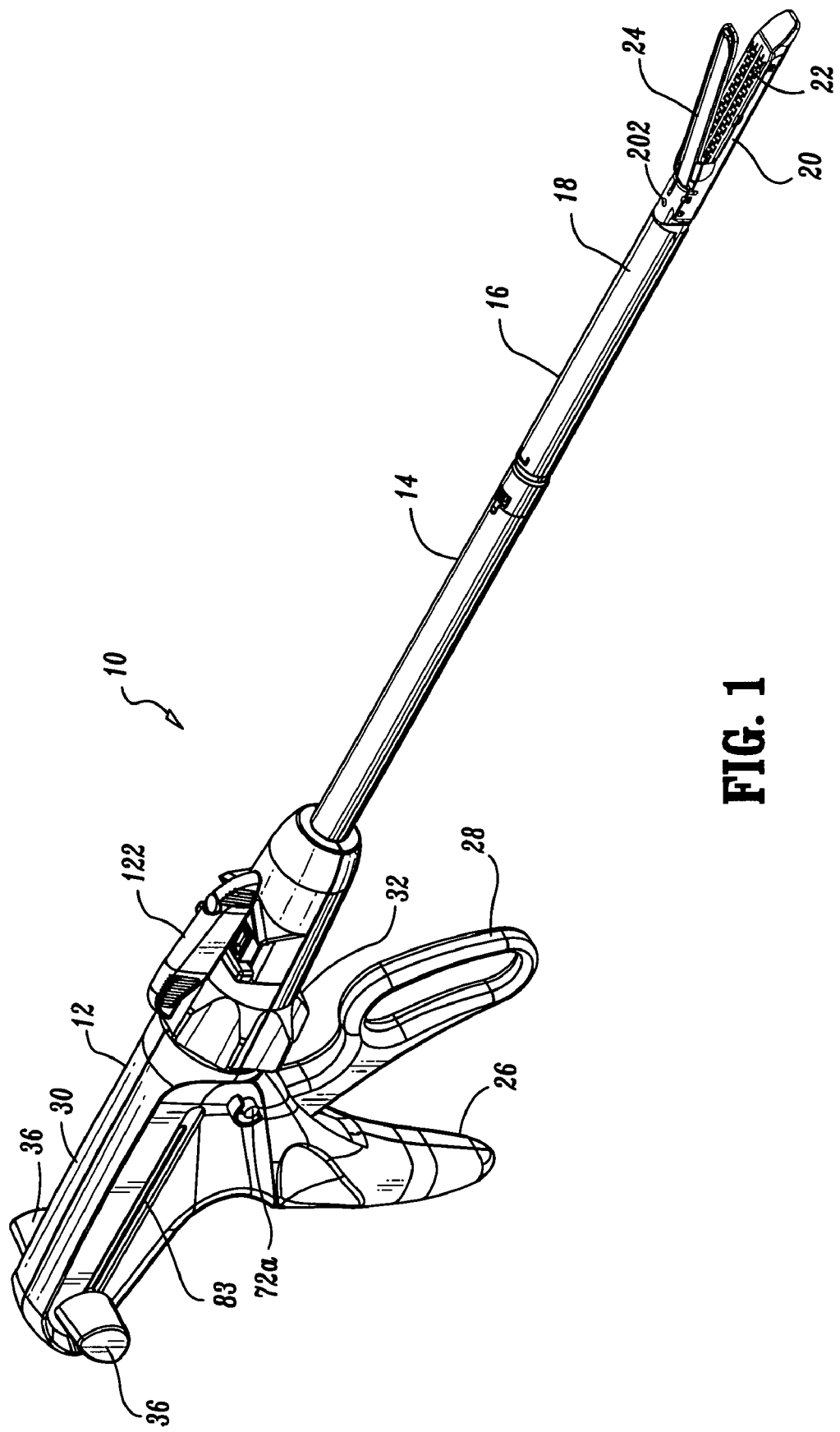
FIG. 1 is a perspective view of a surgical stapling device in accordance with an embodiment of the present disclosure.

Preferred embodiments of the presently disclosed surgical stapling device will now be described in detail with reference to the drawings in which like reference numerals designate identical or corresponding elements in each of the several views.

In the description that follows, the term "proximal" will refer to the end of the stapling device which is closest to the operator, while the term "distal" will refer to the end of the device which is furthest from the operator.

FIGS. 1-23 illustrate one preferred embodiment of the presently disclosed surgical stapling device shown generally as 10. Briefly, surgical stapling device 10 includes a handle assembly 12 and an elongated body 14. The length of elongated body 14 may vary to suit a particular surgical procedure. The elongated body 14 defines a longitudinal axis for the device 10. A replaceable loading unit or DLU 16 is releasably secured to a distal end of elongated body 14. Loading unit 16 includes a proximal body portion 18, which forms an extension of elongated body 14, a distal tool assembly 20 including a cartridge assembly 22, and an anvil assembly 24. Tool assembly 20 is pivotably connected to body portion 18 about an axis substantially perpendicular to the longitudinal axis of elongated body 14. Cartridge assembly 22 houses a plurality of staples. Anvil assembly 24 is movable in relation to cartridge assembly 22 between an open position spaced from cartridge assembly 22 and an approximated or clamped position in juxtaposed alignment with cartridge assembly 24. The staples are housed in cartridge assembly 22 to apply rows of staples in body tissue. For example, in the embodiment shown, the rows of staples are linear rows of staples which may have a length measuring from about 30 mm to about 60 mm. Other staple configurations and lengths are envisioned.

Handle assembly 12 includes a stationary handle member 26, a movable handle or trigger 28 and a barrel portion 30. A rotatable member 32 is preferably rotatably mounted to the forward end of barrel portion 30 and secured to elongated body 14 to facilitate rotation of elongated body 14 in relation to handle assembly 12. An articulation lever 122 is supported on a distal portion of barrel portion 30 and is operable, in a manner to be described hereafter, to effect articulation of tool assembly 20 with respect to body portion 18 of loading unit 16. A pair of return knobs 36 are movably supported along barrel portion 30.

Referring to FIGS. 4-7, handle assembly 12 includes a housing 38, which is preferably formed from plastic molded housing half-sections 38a and 38b. Alternately, other materials may be used to form the housing including metals, e.g., stainless steel. Housing 38 forms stationary handle 26 and barrel portion 30 of handle assembly 12 (see FIG. 1). Movable handle 28 is rotatably supported between housing half-sections 38a and 38b about a cylindrical member 40 which is received within an opening 41 in movable handle 28. A biasing member 42, which is preferably a torsion spring, urges movable handle 28 away from stationary handle 26 to a non-compressed position. Movable handle 28 includes a pair of throughbores 46 dimensioned to receive a pivot member 47. A pawl 48 is rotatably supported on pivot member 47 and is biased by a spring 50 towards actuation shaft 52.

Actuation shaft 52 is slidably supported between retracted and advanced positions within barrel portion 30 of housing 38 and includes a distal end defining a recess 54 configured to rotatably receive the proximal end 56 of firing rod 58. A spring biased retract arm 57 is rotatably mounted between housing half-sections 38a and 38b and includes an extension 57a. Extension 57a is positioned within a slot 59 (FIG. 4) formed in actuation shaft 52 to urge actuation shaft 52 to a fully retracted position. Actuation shaft 52 includes a toothed rack 60. Pawl 48 has an engagement finger 62 which is biased by spring 50 towards toothed rack 60 of actuation shaft 52.

When movable handle 28 is actuated, i.e., is compressed towards stationary handle 26 against the bias of spring 42, engagement finger 62 of pawl 48 engages toothed rack 60 of actuation shaft 52 to advance actuation shaft 52 and firing rod 58 distally. Distal end of firing rod 58 engages proximal end of drive assembly 212 of the loading unit 16, when proximal end of loading unit 16 is engaged with elongated body 14 of surgical stapling device 10.

The surgical stapling device includes a disposable loading unit or "DLU." A loading unit having the desired staple size or sizes, and the desired staple line length, is assembled with the device. The loading units can include a tool assembly that can articulate with respect to the proximal body portion, or loading units that do not provide articulation. The loading units can include tool assemblies having linear rows of staples or other staple configurations. After firing staples from a loading unit, the loading unit can be removed from the device and a new loading unit may be assembled with the device.

Referring to FIGS. 1 and 7-9, a loading unit with an articulating tool assembly is shown. Loading unit 16 includes a tool assembly 20, a proximal body portion 18 and a mounting assembly 202 (FIG. 10). Body portion 18 has a proximal end adapted to releasably engage the distal end of the elongated body 14 in the manner to be discussed in detail below. Mounting assembly 202 is pivotally secured to a distal end of body portion 18 and is fixedly secured to a proximal end of tool assembly 20. Pivotal movement of mounting assembly 202 pivots the tool assembly 20 so that a longitudinal axis of the tool assembly 20 is angled with respect to the longitudinal axis of the elongated body 14. Pivotal movement of mounting assembly 202 about an axis substantially perpendicular to the longitudinal axis of the elongated body 14 effects articulation of tool assembly 20 between a non-articulated position in which the longitudinal axis of tool assembly 20 is aligned with the longitudinal axis of elongated body 14 and an articulated position in which the longitudinal axis of tool assembly 20 is disposed at an angle to the longitudinal axis of elongated body 14.

Figure 7:
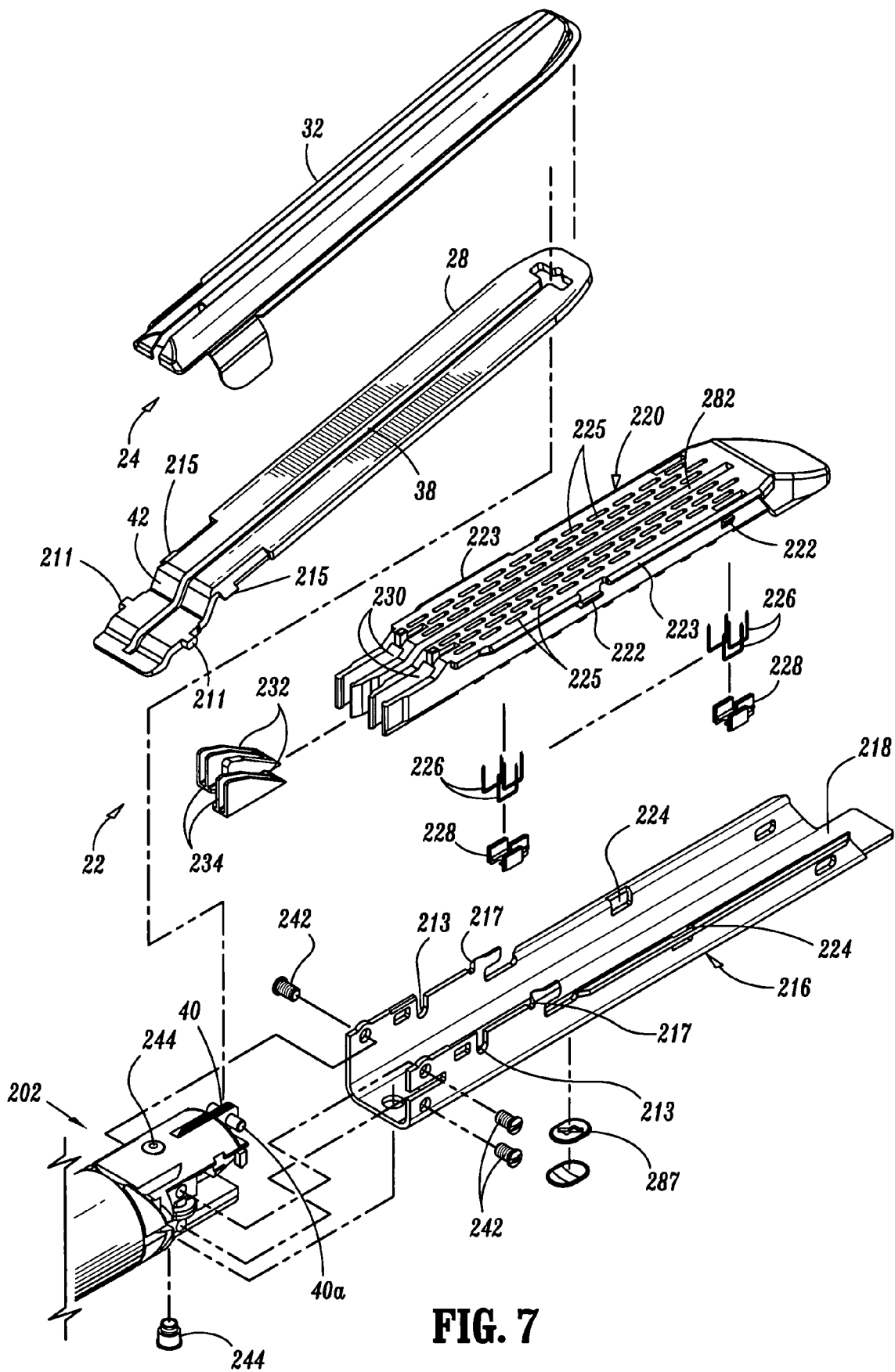
FIG. 7 is a partial, exploded perspective view of the DLU for the surgical stapling device of FIGS. 1-6.
Figure 8:
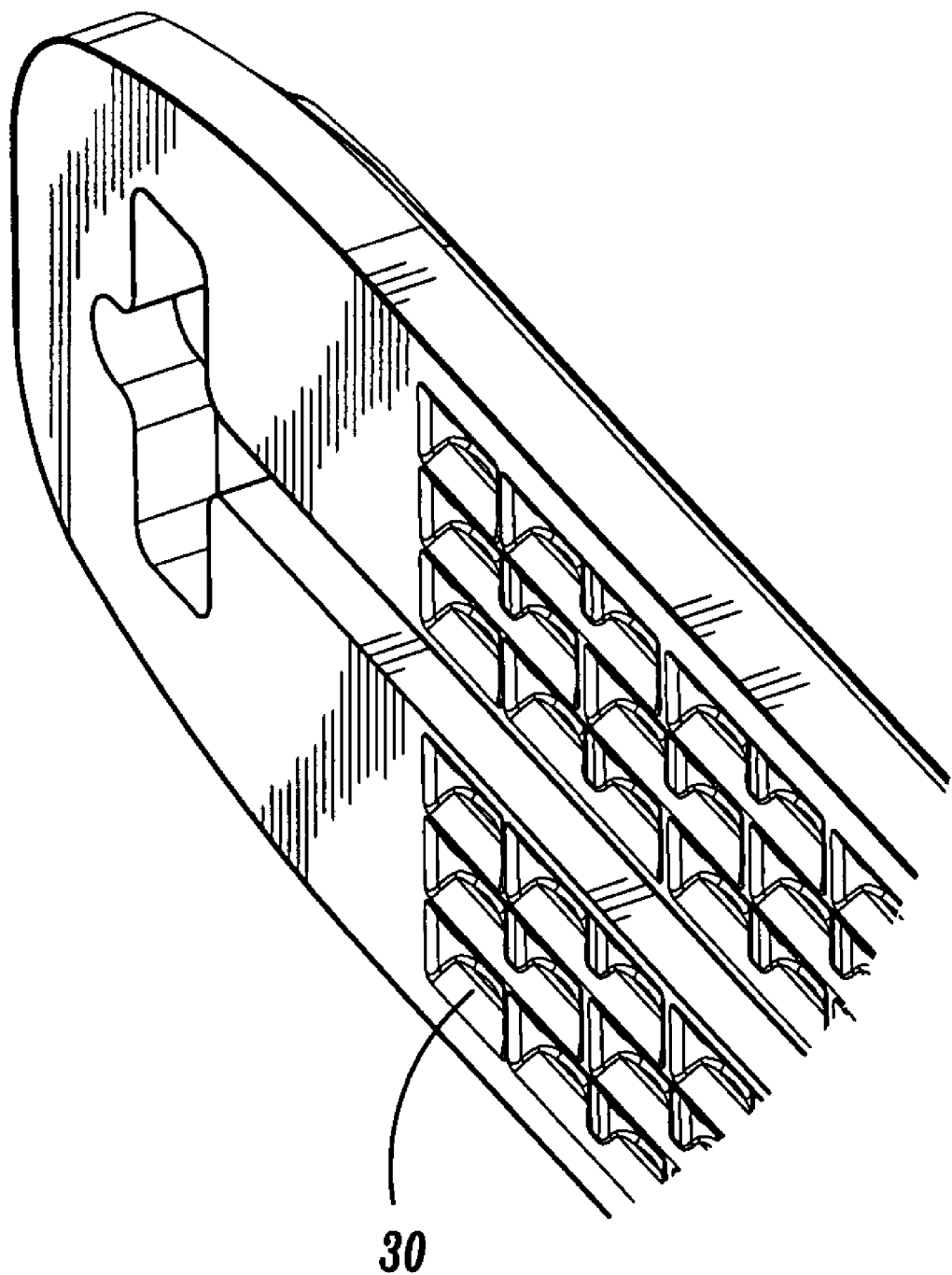
FIG. 8 is a partial perspective view of the anvil member of the surgical stapling device of FIGS. 1-7.
Figure 9:
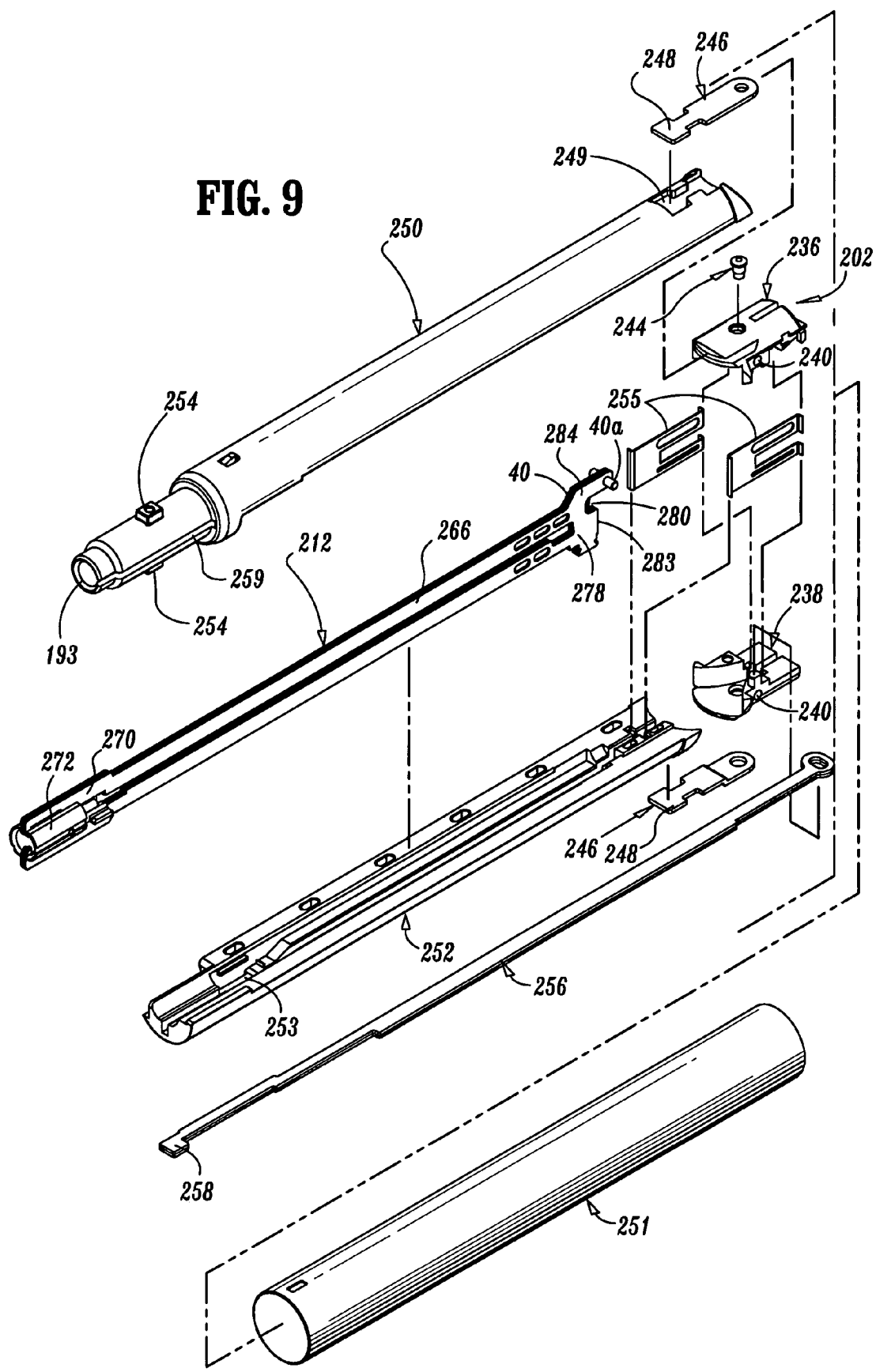
FIG. 9 is a partial, exploded perspective view of the DLU for the surgical stapling device of FIGS. 1-8.
Figure 10:
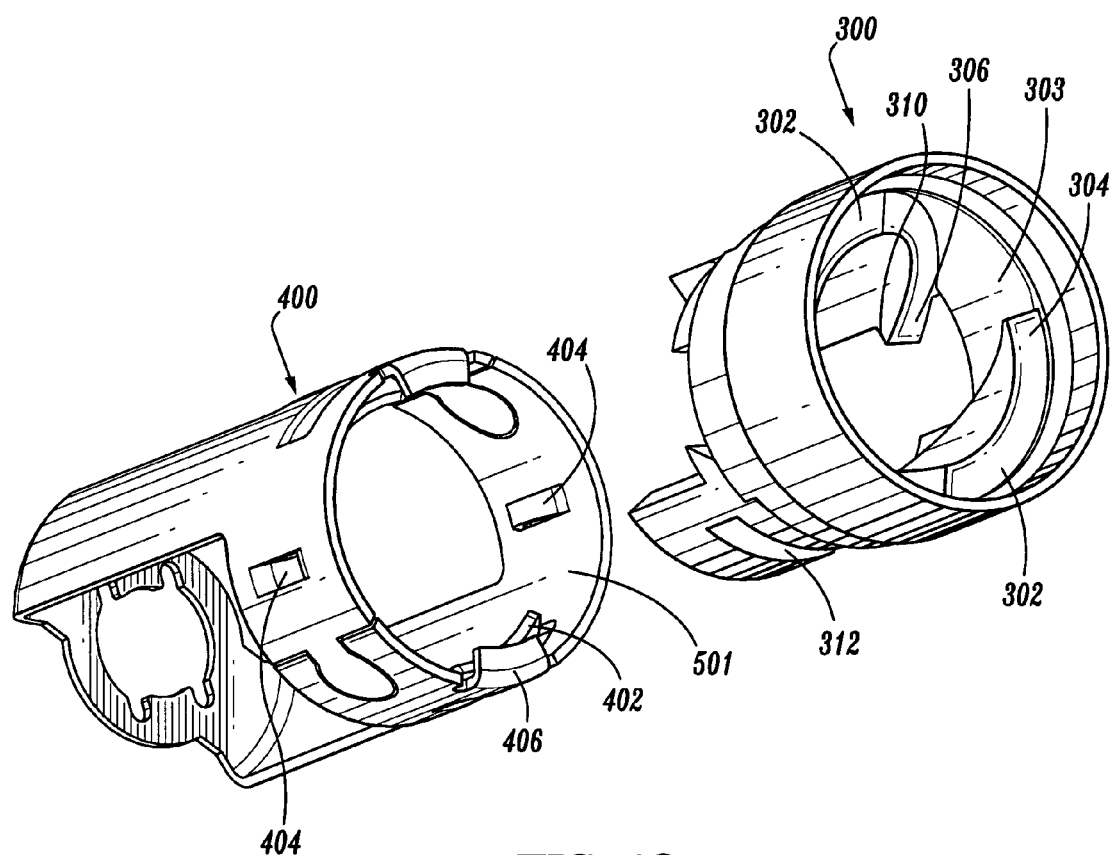
FIG. 10 is an exploded, perspective view of the tip assembly for the surgical stapling device of FIGS. 1-9.

Referring to FIGS. 7-9, tool assembly 20 includes a cartridge assembly 22 and an anvil assembly 24. Anvil assembly 20 includes an anvil portion 28 having a plurality of staple deforming concavities 30 (FIG. 9) and a cover plate 32 secured to a top surface of anvil portion 28. Cover plate 32 and anvil portion 28 define a cavity 34 therebetween. Cover plate 32 prevents pinching of tissue during actuation of loading unit 16 and advancement of the drive assembly 212 through the loading unit 16. A longitudinal slot 38 extends through anvil portion 28 to facilitate passage of a retention flange 40 of drive assembly 212. A camming surface 42 formed on anvil portion 28 is positioned to be engaged by a pair of cam members 40a supported on retention flange 40 of drive assembly 212 to effect approximation of the anvil and cartridge assemblies. A pair of pivot members 211 and a pair of stabilization members 215 are formed on the anvil portion 28.

Cartridge assembly 22 includes carrier 216 which defines an elongated support channel 218 which is dimensioned and configured to receive staple cartridge 220. Carrier 216 has a pair of shoulders 217 and a pair of slots 213 defined in the carrier 216. The pair of slots 213 receives the pair of pivot members 211 to allow the anvil portion 28 to pivot with respect to the cartridge assembly 22. Each of the pair of stabilization members 215 engages a respective shoulder 217 to prevent the anvil portion 28 from sliding axially in relation to the staple cartridge 220 as the anvil portion 28 is pivoted about the pivot members 211. Corresponding tabs 222 and slots 224 formed along staple cartridge 220 and elongated support channel 218, respectively, function to retain staple cartridge 220 at a fixed location within support channel 218. A pair of support struts 223 formed on staple cartridge 220 are positioned to rest on side walls of carrier 216 to further stabilize staple cartridge 220 within support channel 218.

Staple cartridge 220 includes retention slots 225 (FIG. 7) for receiving a plurality of staples or fasteners 226 and pushers 228. A plurality of laterally spaced apart longitudinal slots 230 extend through staple cartridge 220 to accommodate upstanding cam wedges 232 of an actuation sled 234 (FIG. 7). A central longitudinal slot 282 extends along substantially the length of staple cartridge 220 to facilitate passage of the drive assembly 212 (FIG. 9). During operation of surgical stapling device 10, drive assembly 212 is advanced by the firing rod 58. The drive assembly 212 abuts actuation sled 234 and pushes actuation sled 234 through longitudinal slots 230 of staple cartridge 220 to advance cam wedges 232 into sequential contact with pushers 228. Pushers 228 translate vertically along cam wedges 232 within fastener retention slots 225 and urge fasteners 226 from retention slots 225 into staple deforming cavities 206 (FIG. 8) of anvil assembly 24.

The drive assembly 212 includes a drive beam 266 with a working head 268. The distal end of working head 268 of drive beam 266 is defined by a vertical support strut 278 (FIG. 9) which supports a knife blade 280, and an abutment surface 283 which engages a portion of actuation sled 234 during a stapling procedure. Knife blade 280 is positioned to translate slightly behind the actuation sled 234 through a central longitudinal slot 282 in staple cartridge 220 to form an incision between rows of stapled body tissue. A retention flange 40 projects distally from vertical strut 278 and supports a cylindrical cam roller 40a at its distal end. Cam roller 40a is dimensioned and configured to engage cam surface 42 on anvil portion 28 to clamp anvil portion 28 against body tissue.

In use, the user manipulates handle assembly 12 to clamp tissue and fire staples. To approximate the cartridge and anvil assemblies 22 and 24 and clamp tissue, movable handle 28 is moved in the direction toward stationary handle member 26. Movable handle 28 is compressed towards stationary handle 26 against the bias of torsion spring 42 to engage actuation shaft 52. The engagement finger 62 of pawl 48 engages the toothed rack 60 of actuation shaft 52 to advance actuation shaft 52 and firing rod 58 distally.

Firing rod 58 is connected at its distal end to axial drive assembly 212 including drive beam 266, such that advancement of firing rod 58 effects advancement of drive beam 266. As drive beam 266 is advanced, cam roller 40a moves into engagement with cam surface 42 of anvil portion 28 to urge anvil portion 28 in the direction of the cartridge 220 to approximate cartridge and anvil assemblies 22 and 24 and clamp tissue therebetween.

After movable handle 28 is actuated to approximate cartridge and anvil assemblies 22 and 24, biasing member 42 returns handle to its non-compressed position spaced from stationary handle 26.

To fire stapling device 10 once tissue is clamped, the movable handle 28 is moved toward stationary handle member 26 through an actuation stroke during which, engagement finger 62 of pawl 48 engages toothed rack 60 of actuation shaft 52 to further advance actuation shaft 52 and firing rod 58 distally. More than one actuation stroke may be required to fire all the staples from the loading unit 16. As firing rod 58 is advanced in the manner discussed above, drive beam 266 is advanced distally and engages actuation sled 234 through staple cartridge 22 to simultaneously sever tissue with knife 280 and drive pushers 228 to sequentially eject staples 226 from the cartridge. Loading units having staple lines of different lengths may be used and the number of actuating strokes will vary accordingly. The structure and operation of the tool assembly may be in accordance with certain embodiments disclosed in U.S. Pat. No. 5,865,361, the disclosure of which is hereby incorporated by reference herein.

Figure 5:
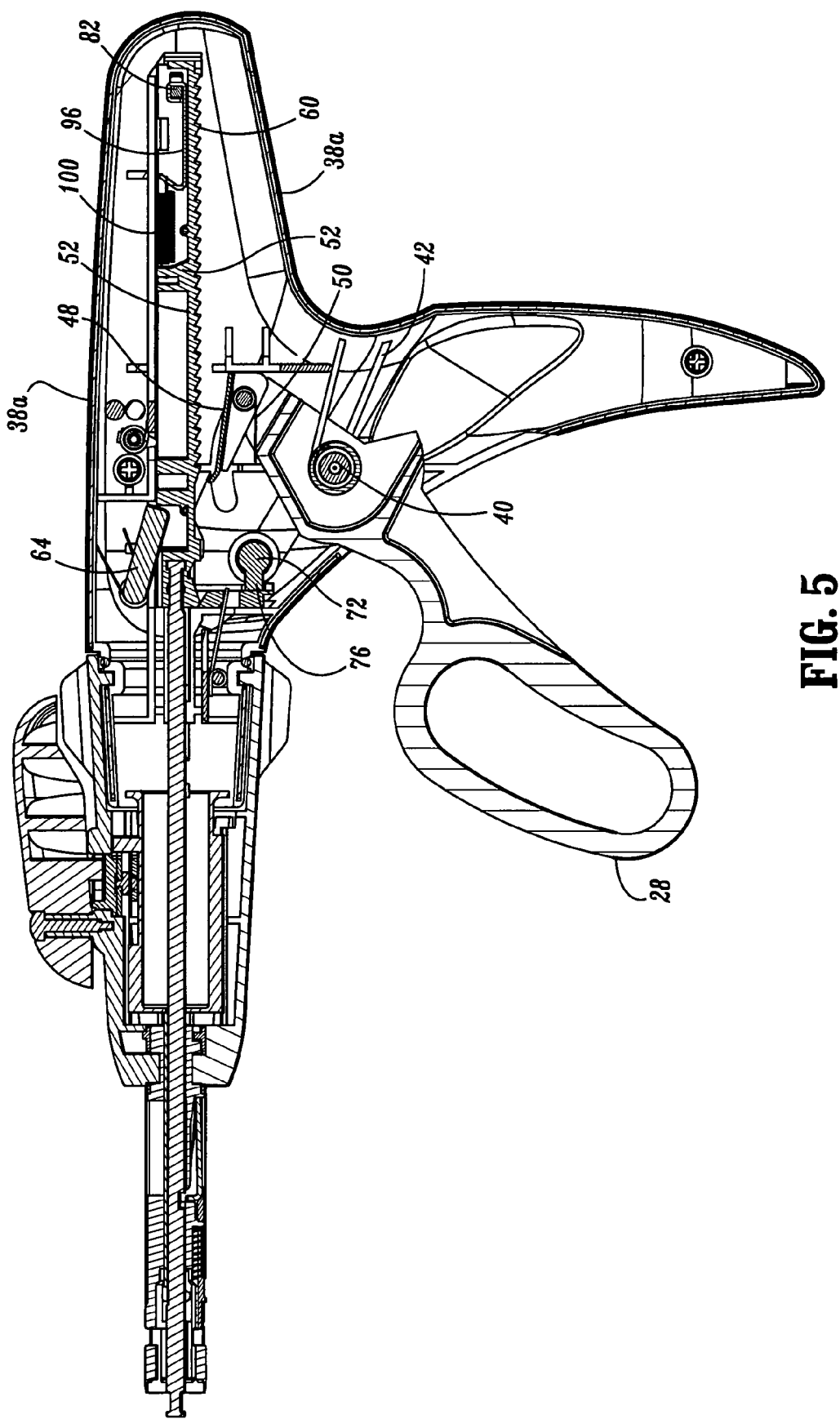
FIG. 5 is a partial cross-sectional view of the surgical stapling device of FIGS. 1-4.
Figure 6:
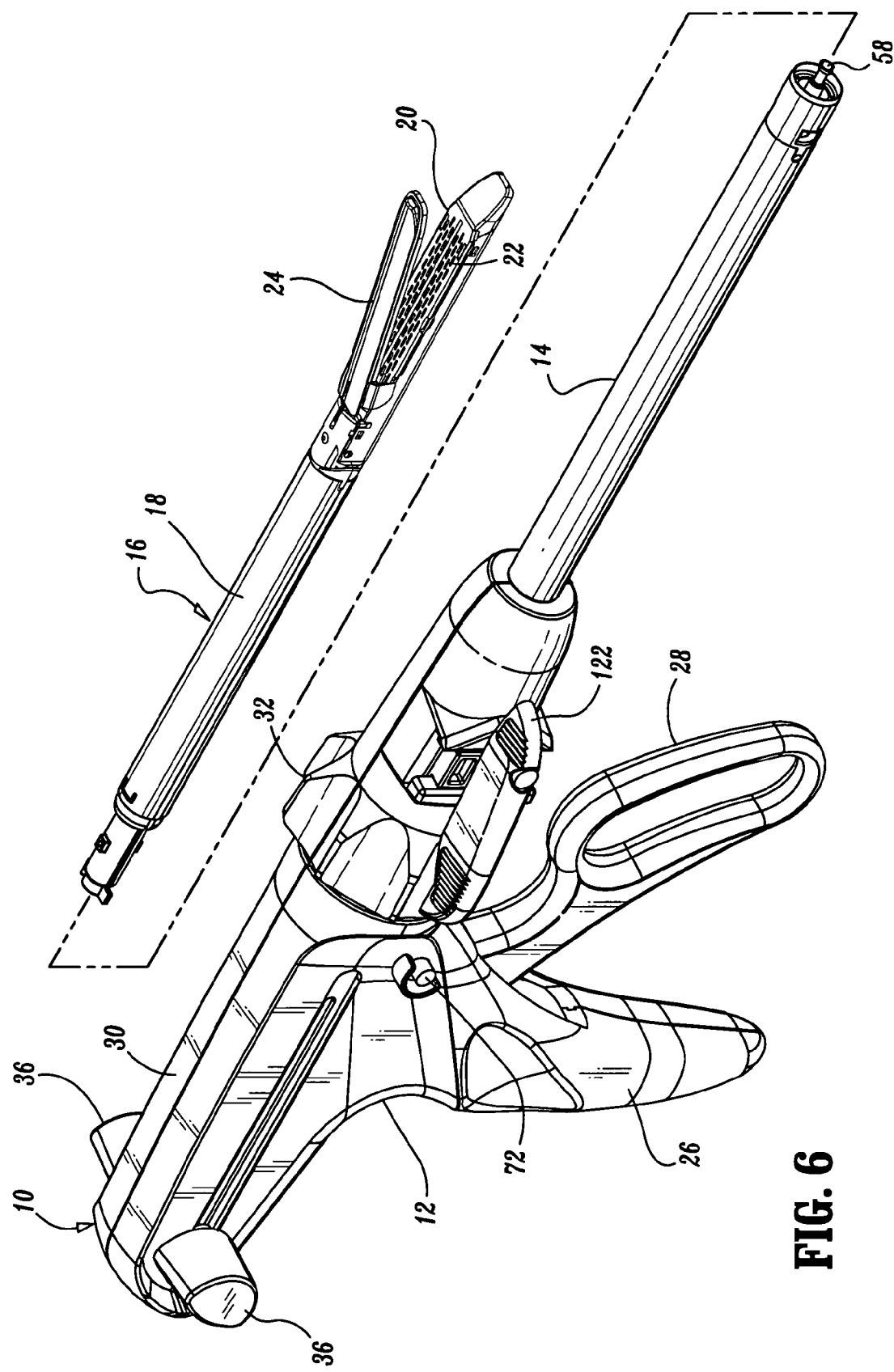
FIG. 6 is a perspective view of the surgical stapling device of FIGS. 1-5, showing the DLU separated from the device.

The elongated body 14 is mounted in a rotatable member 32 as shown in FIG. 5 and the rotatable member 32 is attached to the handle assembly 12 so as to allow the elongated body 14 and loading unit 16, including the tool assembly 20, to rotate around the longitudinal axis. The rotatable member 32 is formed from one or more tubular or conical members and houses an articulation actuation mechanism for articulating the tool assembly 20 with respect to the longitudinal axis of the device 10. The articulation actuation mechanism includes an articulation lever 122 (FIG. 6). The articulation lever 122 is operably connected to an articulation arm extending through the elongated body 14. The articulation lever 122 may be connected to a mechanism for defining predetermined degrees of articulation of the tool assembly 20. The operation and structure of the articulation lever 122 may be as described in U.S. Published Patent Application No. 2004/0232201, the disclosure of which is hereby incorporated by reference herein. The articulation lever 122 is mounted on the rotatable member 32 about a pivot pin and is attached to an articulation arm so that rotation of the lever 122 about the pivot pin effects longitudinal motion of the articulation arm. The articulation arm extends through the elongated body 14 and is attached to an articulation link 256 of the loading unit 16 (FIG. 9) when the loading unit 16 is mounted on the elongated body 14. The articulation lever 122 can be rotated by the user of the surgical stapling device 10 to articulate the tool assembly 20. As the articulation lever 122 is rotated in a first direction, the articulation arm attached to the lever is advanced in the distal direction. The articulation arm advances the articulation link 256 of the loading unit 16 and pivots the mounting assembly 202 about pivot 244 to articulate the tool assembly 20 in the first direction. As the articulation lever 122 is rotated in a second direction, the articulation arm attached to the lever is retracted in the proximal direction. The articulation arm retracts the articulation link 256 of the loading unit 16 and pivots the mounting assembly 202 about pivot 244 to articulate the tool assembly 20 in the second direction.

As depicted in FIG. 6, the loading unit 16 is removably mounted on the distal end of the elongated body 14. The body portion 18 of the loading unit 16 includes a first housing 250 and a second housing 252 that define a channel 253 for allowing the advancement of the axial drive assembly 212. (FIG. 9). The housings 250 and 252 also define a slot for the articulation link 256. The housings 250 and 252 are received in an outer tube 251. The proximal ends of the housings 250 and 252 define an insertion tip 193 on which is formed a pair of lugs 254. The lugs 254 form a releasable connection with the elongated body 14 so that the loading unit 16 may be mounted on and removed from the elongated body 14. A pair of blowout plates 255 are positioned adjacent the distal end of the proximal body portion 18 and adjacent the mounting assembly 202. The blowout plates 255 support the drive assembly 212 during articulation and firing of the tool assembly 20. The structure and operation of the blowout plates 255 are described more fully in U.S. Published Patent Application No. 2004/0232201, the disclosure of which is hereby incorporated by reference herein.

The distal end of the elongated body 14 defines a tip assembly 301 for mounting the loading unit 16 thereon. FIGS. 10-15 and 18 show a tip assembly 301 according to the present disclosure. The tip assembly includes a ring 300 mounted to the distal end of the elongated body 14 so that it is rotationally fixed and a yoke 400 movably mounted to the ring 300. (See FIGS. 10 and 14). The ring 300 defines a passage 303 in which two helical guiding ramps 302 are formed. Each of the guiding ramps has a distal end 304 and a proximal end 306 and a ledge 310 adjacent the proximal end 306. A groove 312 is defined in the inner surface of the ring 300 for mounting the yoke 400 thereon. (See FIG. 10).

Figure 11:
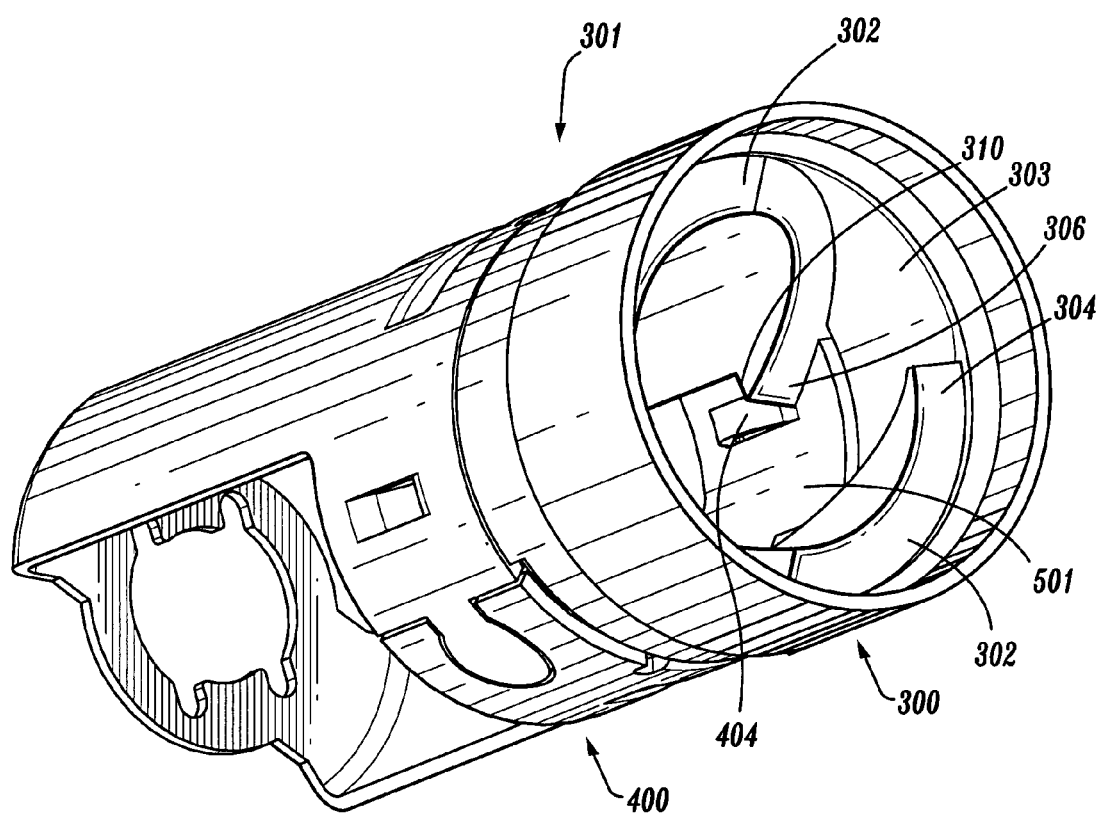
FIG. 11 is a perspective view of the tip assembly for the surgical stapling device of FIGS. 1-10.
Figure 12:
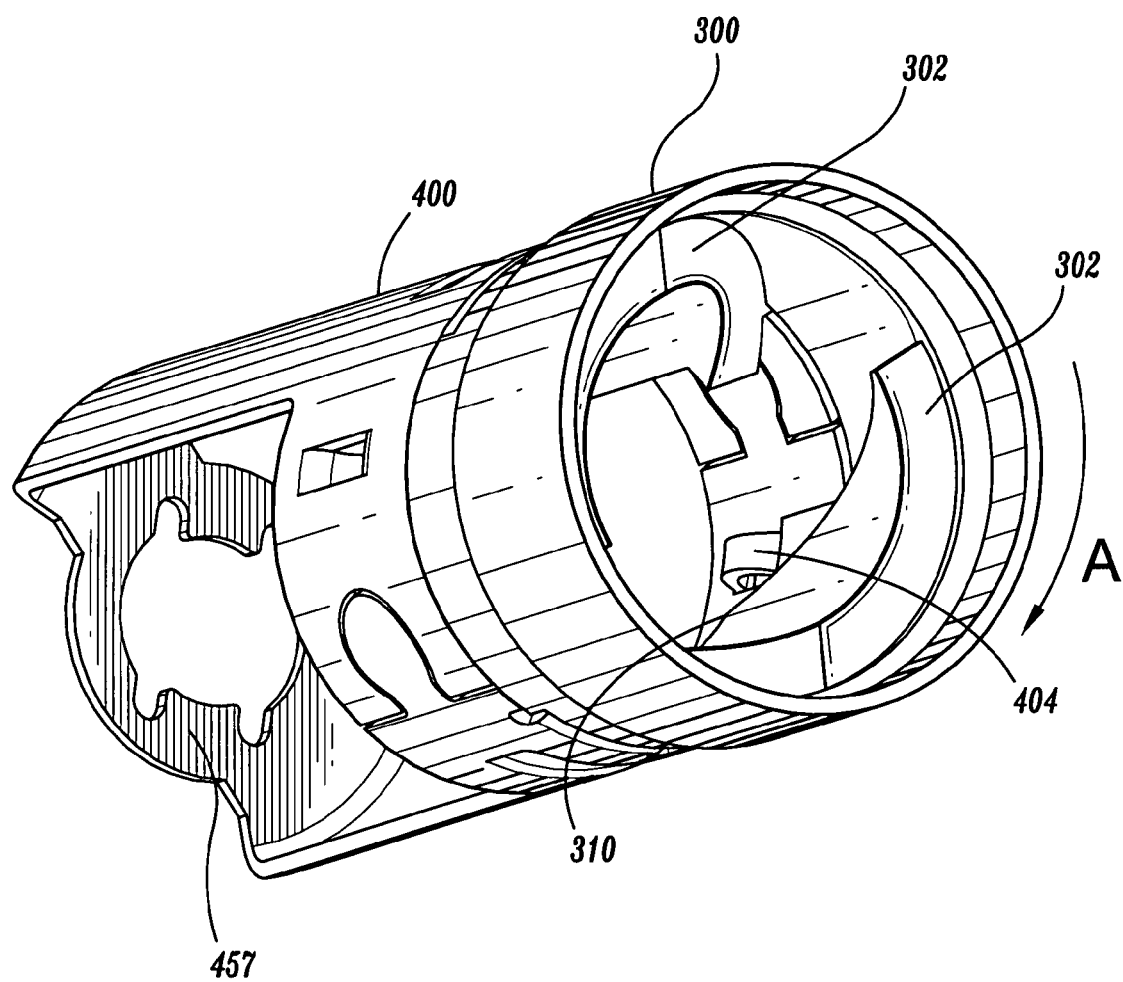
FIG. 12 is a perspective view of the tip assembly for the surgical stapling device of FIGS. 1-11.
Figure 13:
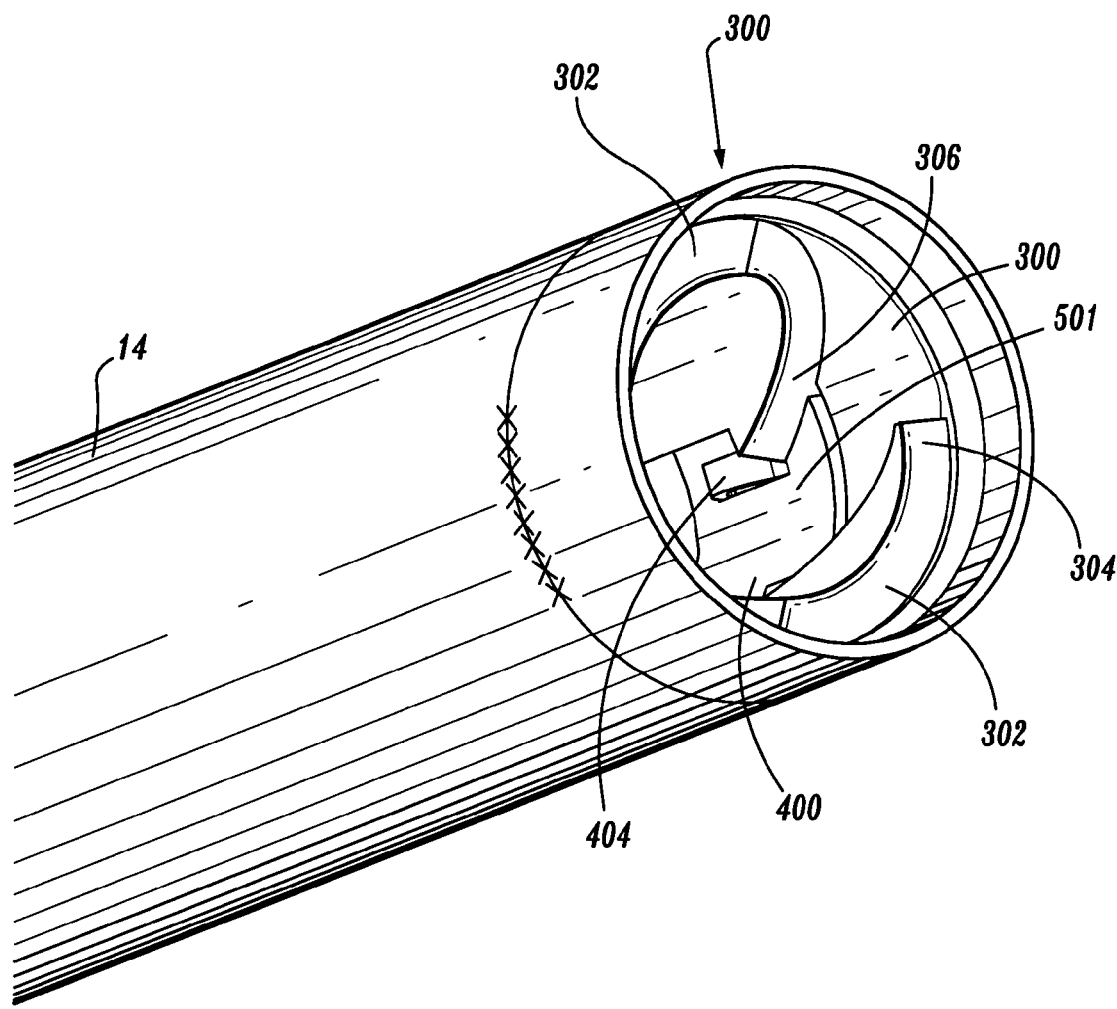
FIG. 13 is a partial perspective view of the elongated body and tip assembly for the surgical stapling device of FIGS. 1-12.

The moveable yoke 400 has at least one protrusion for interacting with the lugs 254 on the loading unit 16. As shown in FIG. 11, the protrusions include two tabs 402 and two stops 404 arranged in pairs so that each tab 402 and stop 404 define a receiving space 501. The distal end of the yoke 400 also has a ridge 406 which cooperates with the groove 312 of the ring 300 so that the yoke 400 is rotatable with respect to the ring 300 from a first, initial position to a second position. As the yoke 400 rotates, the positions of the tabs and stops with respect to the proximal ends 306 of the guiding ramps 302 change. In the first position of the yoke 400 as shown in FIG. 11, a tab 402 and stop 404 pair are disposed adjacent one of the proximal ends 306 of one of the guiding ramps 302, so that receiving space 501 is positioned for receiving one of the lugs 254 of the loading unit 16. In the second position of the yoke 400 as shown in FIG. 12, the tab 402 and stop 404 pair are positioned so that the receiving space 501, and the lug 254 disposed therein, is disposed beneath the ledge 310.

Figure 14:
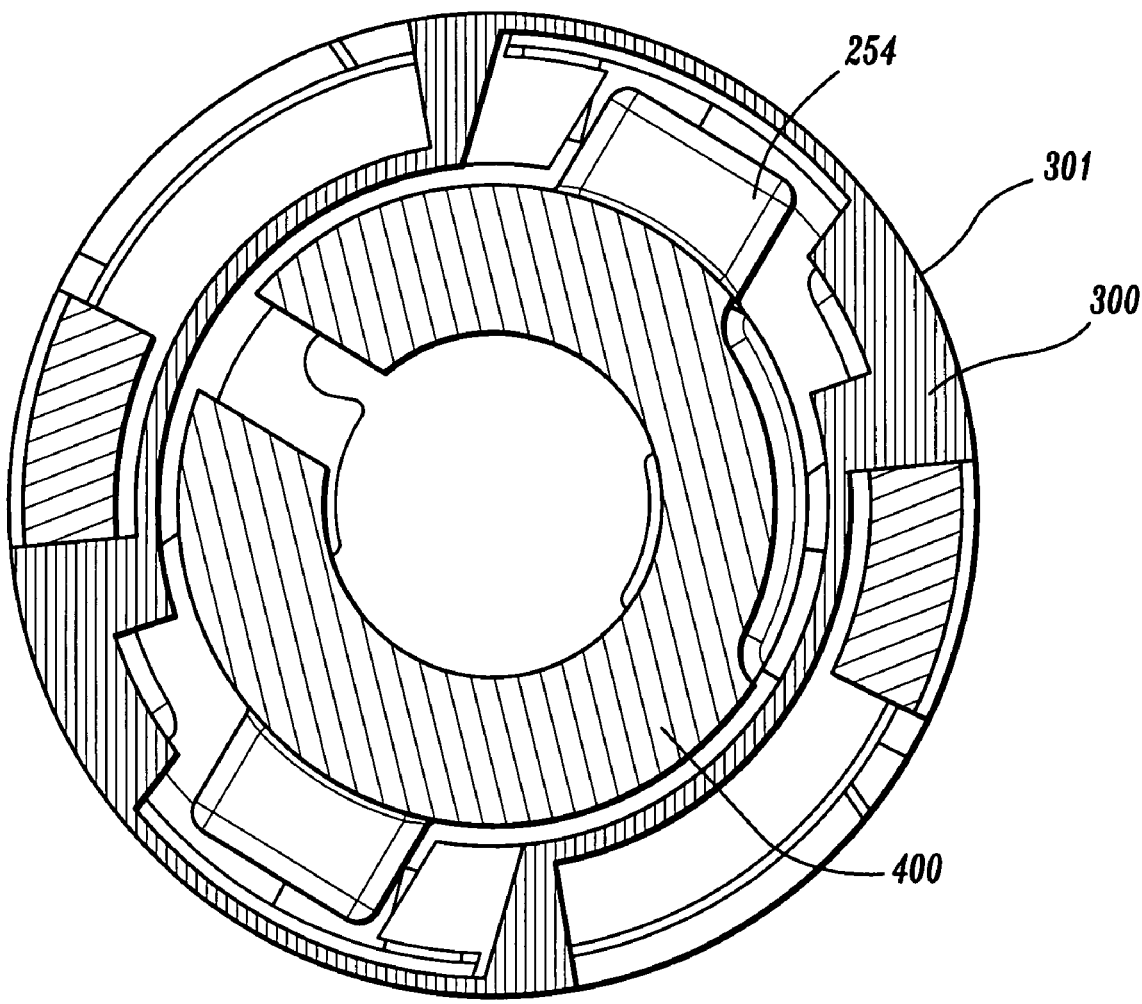
FIG. 14 is a partial, cross-sectional view of the tip assembly and DLU for the surgical stapling device of FIGS. 1-13.
Figure 15:
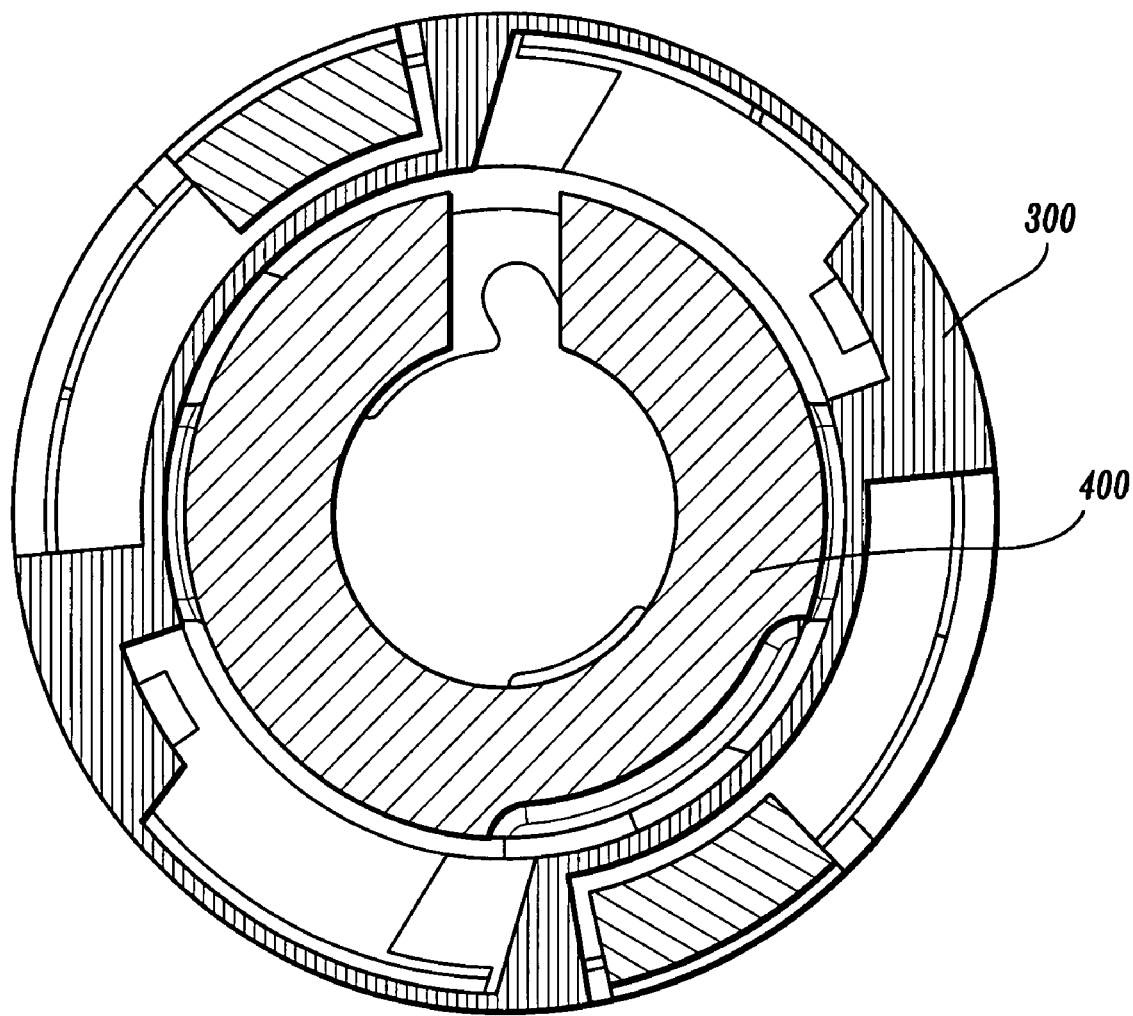
FIG. 15 is a partial, cross-sectional view of the tip assembly and DLU for the surgical stapling device of FIGS. 1-14.
Figure 16:
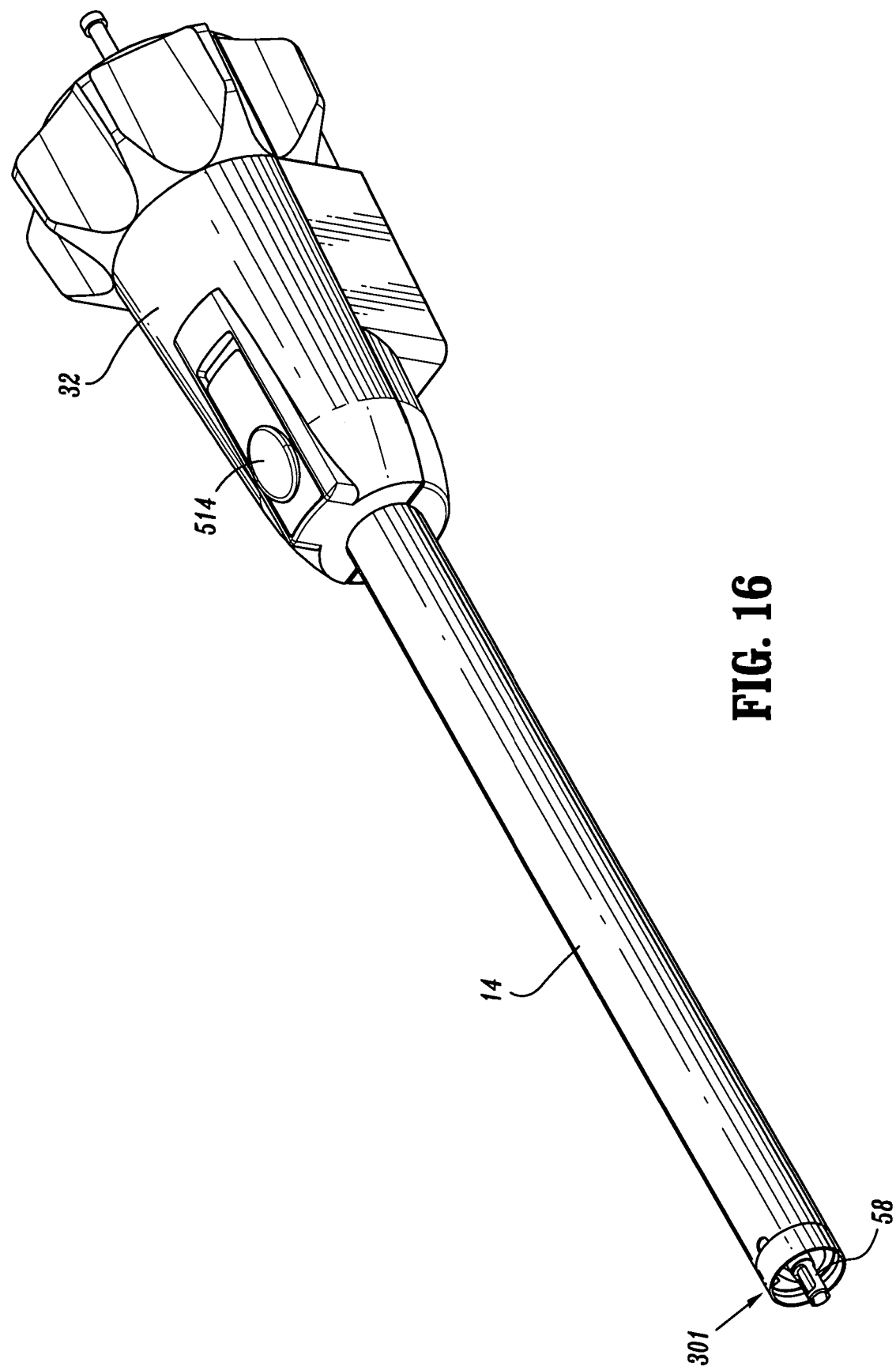
FIG. 16 is a partial, perspective view of the surgical stapling device of FIGS. 1-15 showing the elongated body.
Figure 17:
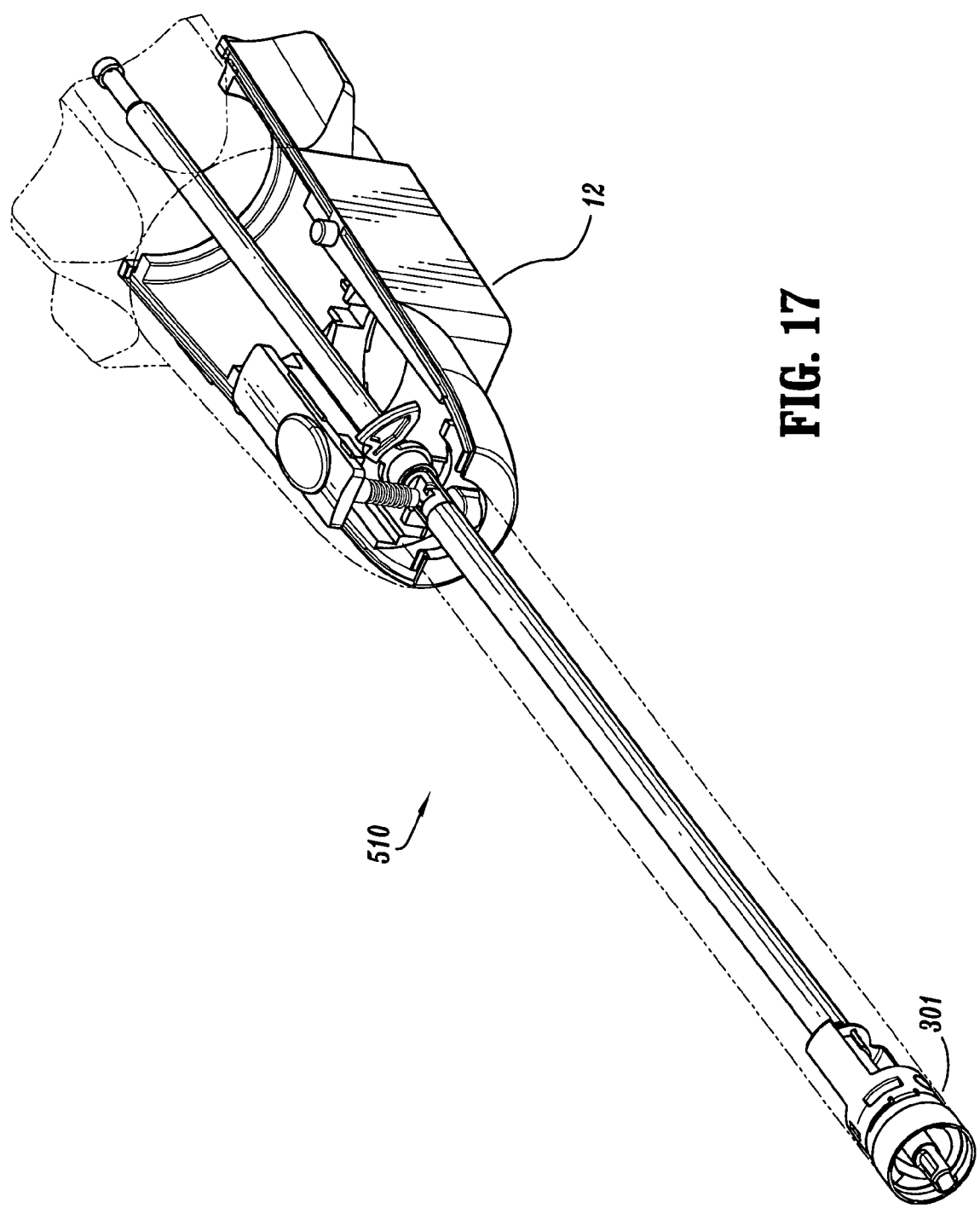
FIG. 17 is a partial, perspective view, with parts removed, of the surgical stapling device of FIG. 16, showing the elongated body.

The loading unit 16 is inserted into the tip assembly 301 so that the insertion tip 193 is inserted into passage 303. The lugs 254 are advanced into the passage 303 of the ring 300 and contact the distal ends 304 of the guiding ramps 302. (See FIG. 11). When the loading unit 16 is rotated in Direction A (see FIG. 12), the lugs 254 are guided on the guiding ramps 302 towards the proximal ends 306 of the guiding ramps 302 and drop into the receiving spaces 501 of the yoke 400. FIG. 14 shows the lugs 254 in the receiving spaces 501. The tip assembly 301 is still in the first position and a stop 404 and tab 408 are disposed on either side of a lug 254, and adjacent a proximal end 306 of one of the guiding ramps 302. In this position, the loading unit 16 may be moved distally and removed from the elongated body 14. The user continues to rotate the loading unit 16 in Direction A, so that lugs 254 push against the tabs 402, thereby rotating moveable yoke 400 into the second position, as shown in FIG. 12. The lugs 254 are situated beneath ledges 310. FIG. 15 shows the lugs 254 positioned beneath ledges 310. The stops 404 prevent the loading unit 16 from rotating with respect to the yoke 400. Thus, the loading unit 16 is captured in the tip assembly 301 and cannot be moved without rotating the yoke 400.

As the loading unit 16 is mounted on to the distal end of the elongated body 14, a distal end of the firing rod 58 is connected to the proximal end of the drive assembly 212. The proximal end of the drive assembly 212 includes a drive member 272 with a porthole for receiving the distal end of the firing rod 58. When the loading unit 16 is rotated during mounting of the loading unit, the articulation link 256 moves into engagement with engagement structure on the distal end of the articulation arm.

To remove the loading unit 16 from the device, the loading unit 16 is rotated in the direction opposite to Direction A, rotating the yoke 400 with it. The lugs 254 are thereby moved away from the ledges 310. The articulation link 256 and the articulation arm are moved away from engagement with one another as the loading unit is rotated. The loading unit 16 can be removed from the device by continuing to rotate the loading unit 16 so that the lugs 254 follow the guiding ramps 302 toward the distal ends 304 and moving the DLU distally. In removing the DLU from the elongated body 14, the firing rod 58 is disengaged from the drive assembly 212.

The surgical stapling device 10 according to the present disclosure includes a sensor mechanism 510 and a locking structure 513, as shown in FIGS. 16-23. The sensor mechanism 510 and the locking structure 513 interact with the tip assembly 301 (FIG. 17) to secure the loading unit 16 onto the elongated body 14. The sensor mechanism 510 and locking structure 513 release the loading unit 16 from the elongated body 14. The locking structure 513 locks the firing rod 58 in position until the loading unit 16 is loaded onto the elongated body 14.

Figure 18:
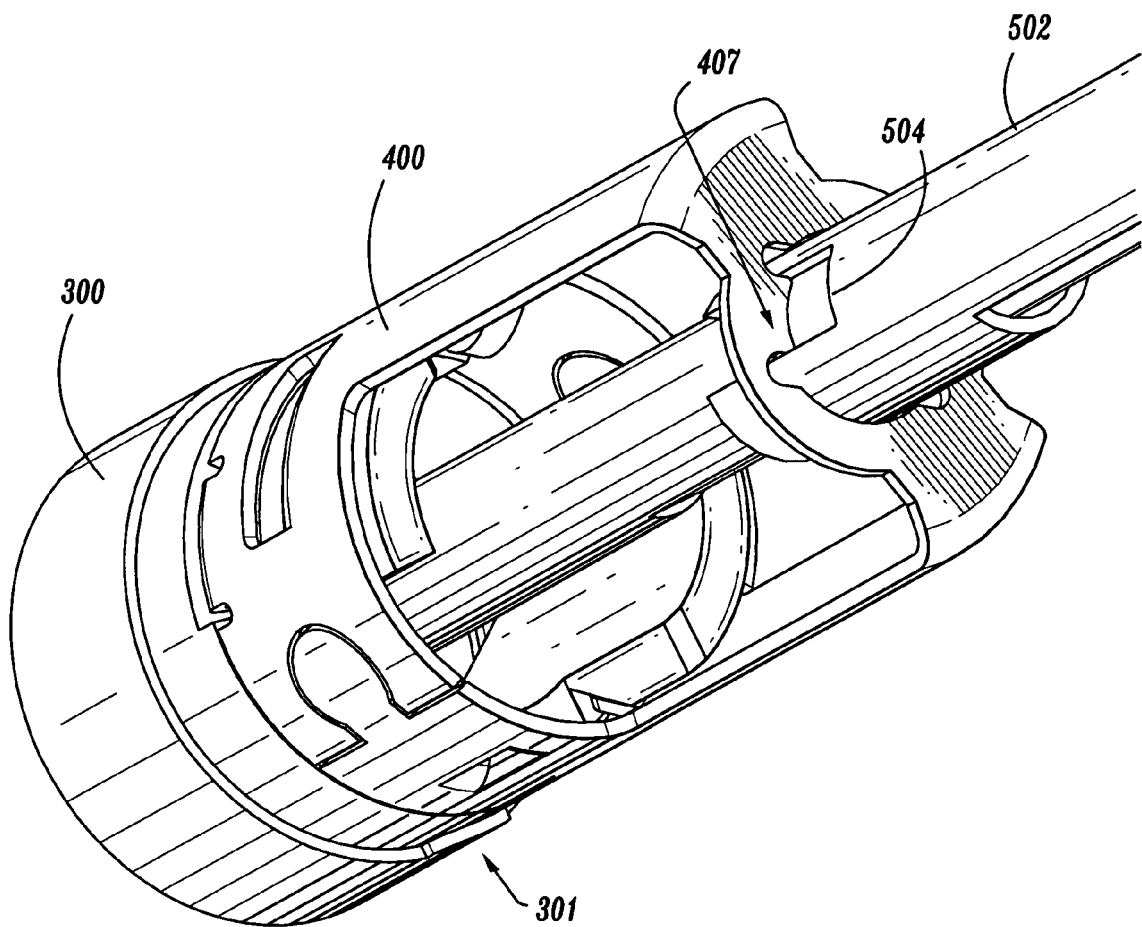
FIG. 18 is a partial perspective view, with parts removed, of the surgical stapling device of FIGS. 1-17, showing the tip assembly.
Figure 19:
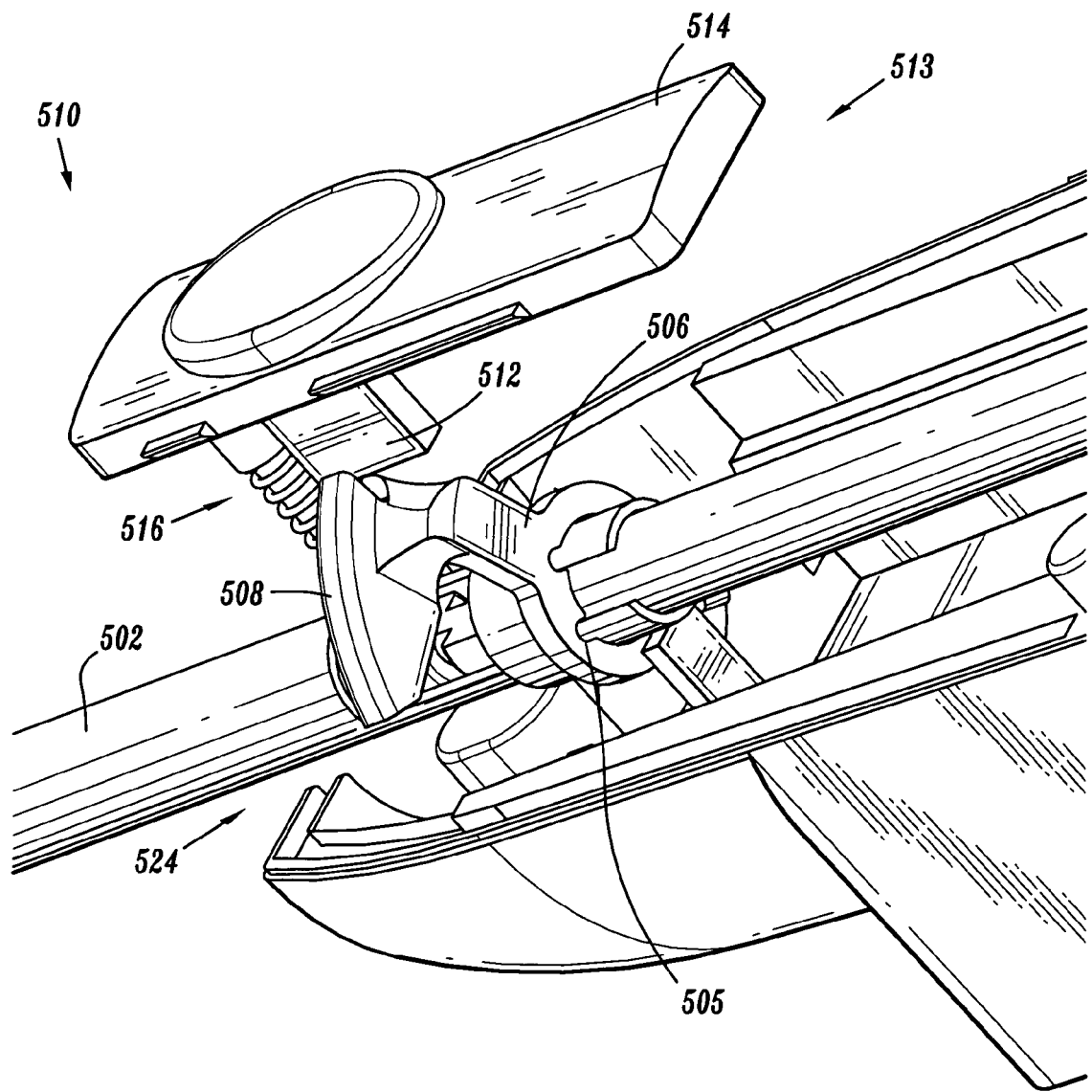
FIG. 19 is a partial perspective view with parts removed of the surgical stapling device of FIGS. 1-18, showing the locking structure.

The sensor mechanism 510 includes a sensor tube 502 having a distal end with a groove 504, as shown in FIG. 18. The yoke 400 of the tip assembly 301 has a protrusion 407 that engages the groove 504 and keys movement of the yoke 400 to the sensor tube 502. As the yoke 400 is rotated during the loading of the loading unit 16, the sensor tube 502 is rotated in the same direction. The proximal end of the sensor tube 502 is connected to the locking structure 513. The locking structure 513 includes a button 514 or other manipulatable actuator at the proximal end of the elongated body 14, or on the handle assembly 12, so that it is accessible to the user of the device 10. For example, the button 514 is shown in FIG. 19 on the rotatable member 32. The button 514 has a button tang 512 that extends toward the sensor tube 502. A release flange 508 is attached to the sensor tube 502 and rotates with the sensor tube 502 from a first position away from button tang 512 (FIG. 20) to a second position in which movement of the release flange 508 is blocked by button tang 512 of locking structure 513 (FIG. 19). The button 514 is biased in the distal direction by a spring.

Figure 23:
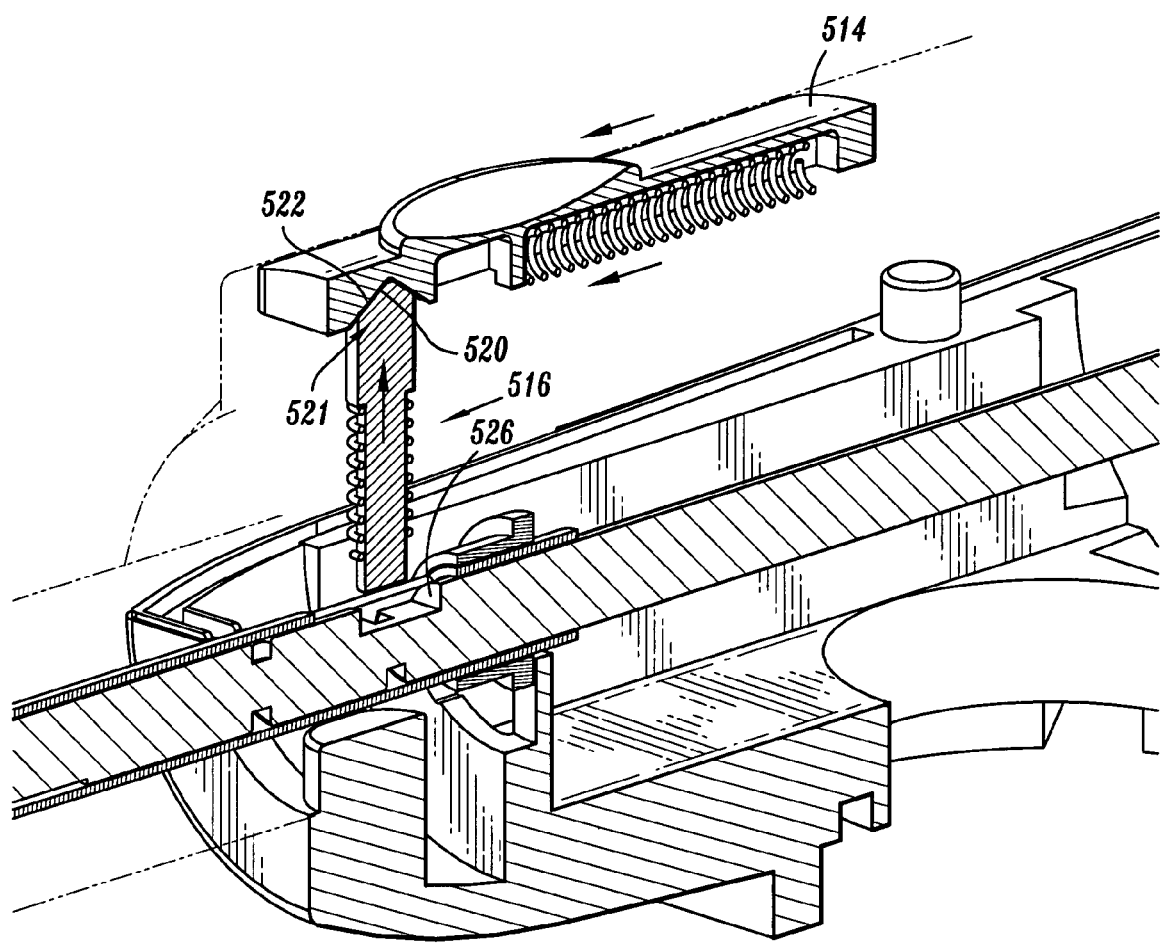
FIG. 23 is a partial cross-sectional view with parts removed of the surgical stapling device of FIGS. 1-22, showing the locking structure.

A plunger 516 interacts with the firing rod 58. The firing rod 58 proximal end 524 has a notch 526 defined therein, as best seen in FIGS. 20-23. The plunger 516 has a first end for engaging the firing rod 58 at the notch 526 and a second end with a beveled surface 522 that is positioned so as to communicate with the button 514 (FIGS. 21 and 23). The plunger 516 is biased in a direction away from the firing rod 58.

In the initial position, before a loading unit 16 is mounted on the device 10, the locking structure 510 engages the firing rod 58 in the notch 526, preventing the advancement of the firing rod 58. The release flange 508 prevents the button 514 from moving distally so that the button 514 maintains the plunger 516 in engagement with the notch 526. When the loading unit 16 is mounted onto the device, the yoke 400 is turned, thereby turning the sensor tube 502. The release flange 508 moves away from button tang 512, allowing the button 514 to move distally. The button 514 allows the plunger 516 to move away from notch 526, as shown in FIG. 23. The locking structure 510 has been disengaged from firing rod 58, allowing the firing rod 58 to move when the moveable handle 28 is manipulated and the device 10 is actuated to clamp tissue and fire staples. The loading unit 16 is also locked onto the device 10, as the release lever 508 is blocked by the button tang 512, preventing rotation of the sensor tube 502. With the sensor tube 502 prevented from rotation, the yoke 400, which holds the loading unit 16 onto the device 10, is prevented from rotation.

Figure 20:
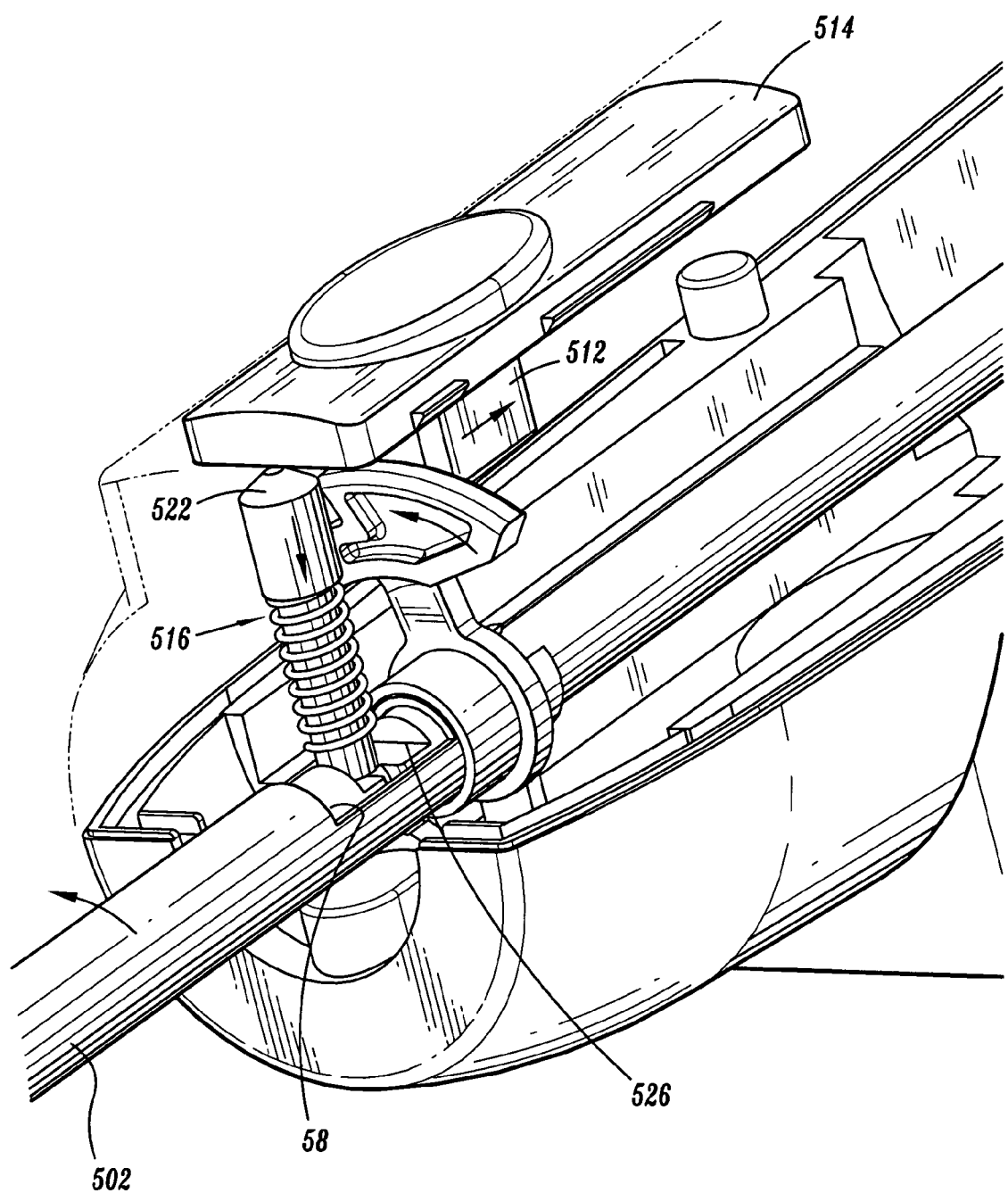
FIG. 20 is a partial perspective view with parts removed of the surgical stapling device of FIGS. 1-19, showing the locking structure.
Figure 21:
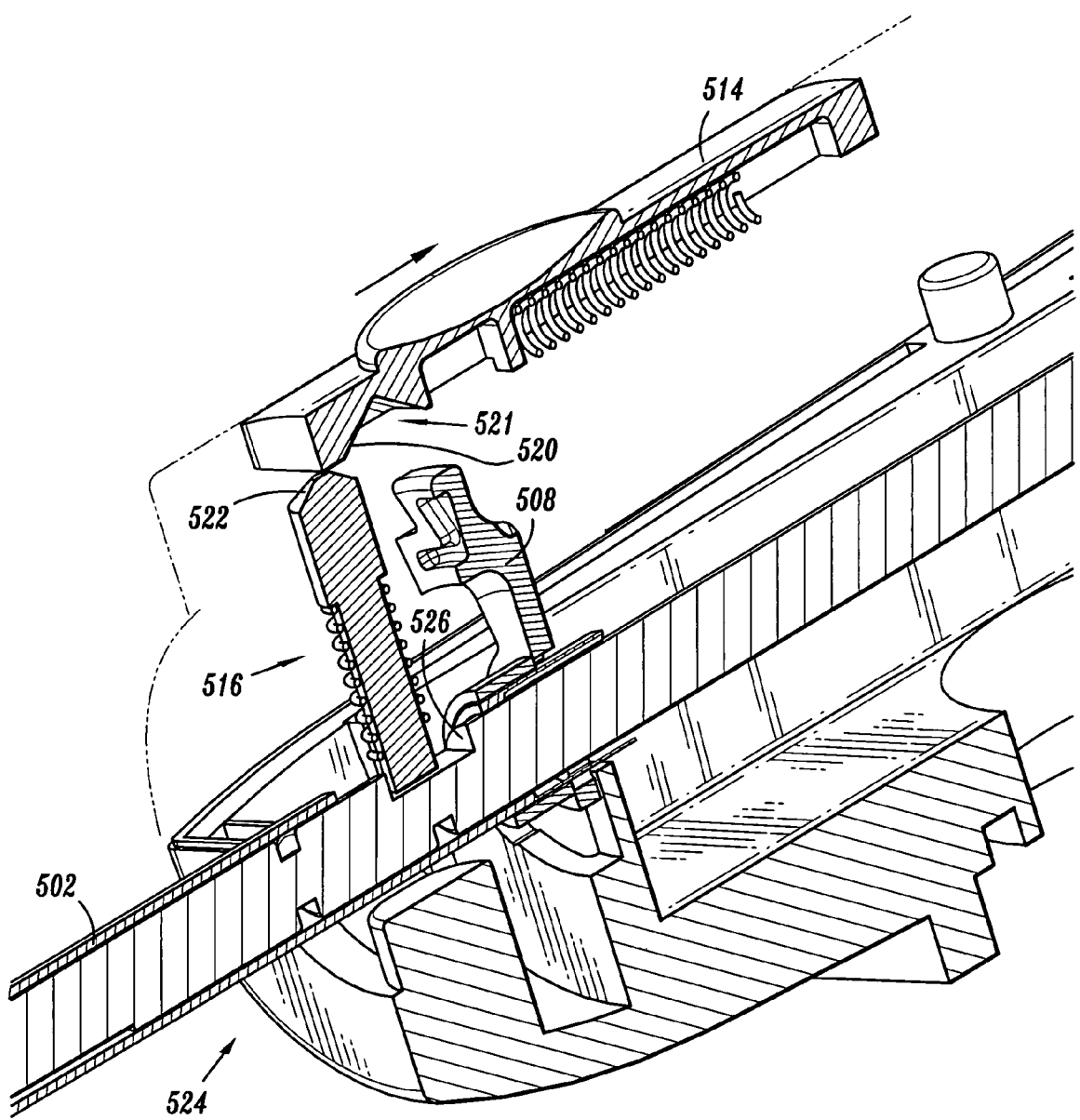
FIG. 21 is a partial cross-sectional view with parts removed of the surgical stapling device of FIGS. 1-20, showing the locking structure.
Figure 22:
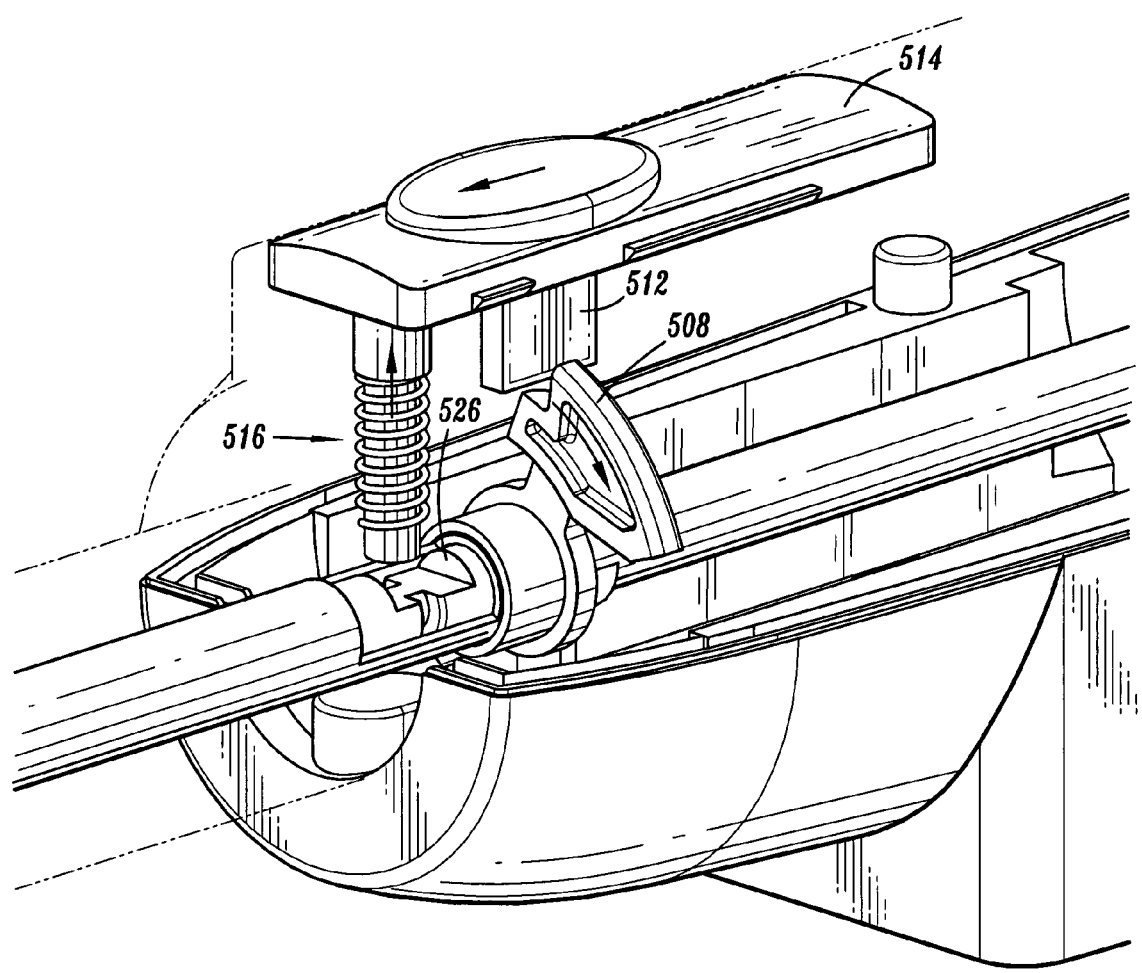
FIG. 22 is a partial perspective view with parts removed of the surgical stapling device of FIGS. 1-21, showing the locking structure.

When the loading unit 16 is to be removed from the device 10, button 514 of locking structure 510 is moved against the bias of the button spring, as shown in FIG. 21, moving button tang 512 away from release flange 508, as shown in FIG. 20. The loading unit 16 can then be rotated and removed from the tip assembly 301 on the elongated body 14. In addition, the locking structure 510 engages the firing rod 58, as the button 514 cams the plunger 516 downwardly into the notch 526, as shown in FIG. 21.

A locking structure and/or sensor mechanism in accordance with the present disclosure may be used to secure any surgical loading unit, such as a staple cartridge, replaceable tool assembly, or other end effector, while providing for the release of the same from a surgical instrument. Desirably, the manipulatable actuator for releasing and/or locking the surgical loading unit is disposed adjacent the handle assembly. In an endoscopic instrument, the manipulatable actuator is disposed at or adjacent to the proximal end of the endoscopic shaft or elongated body.

Figure 4:
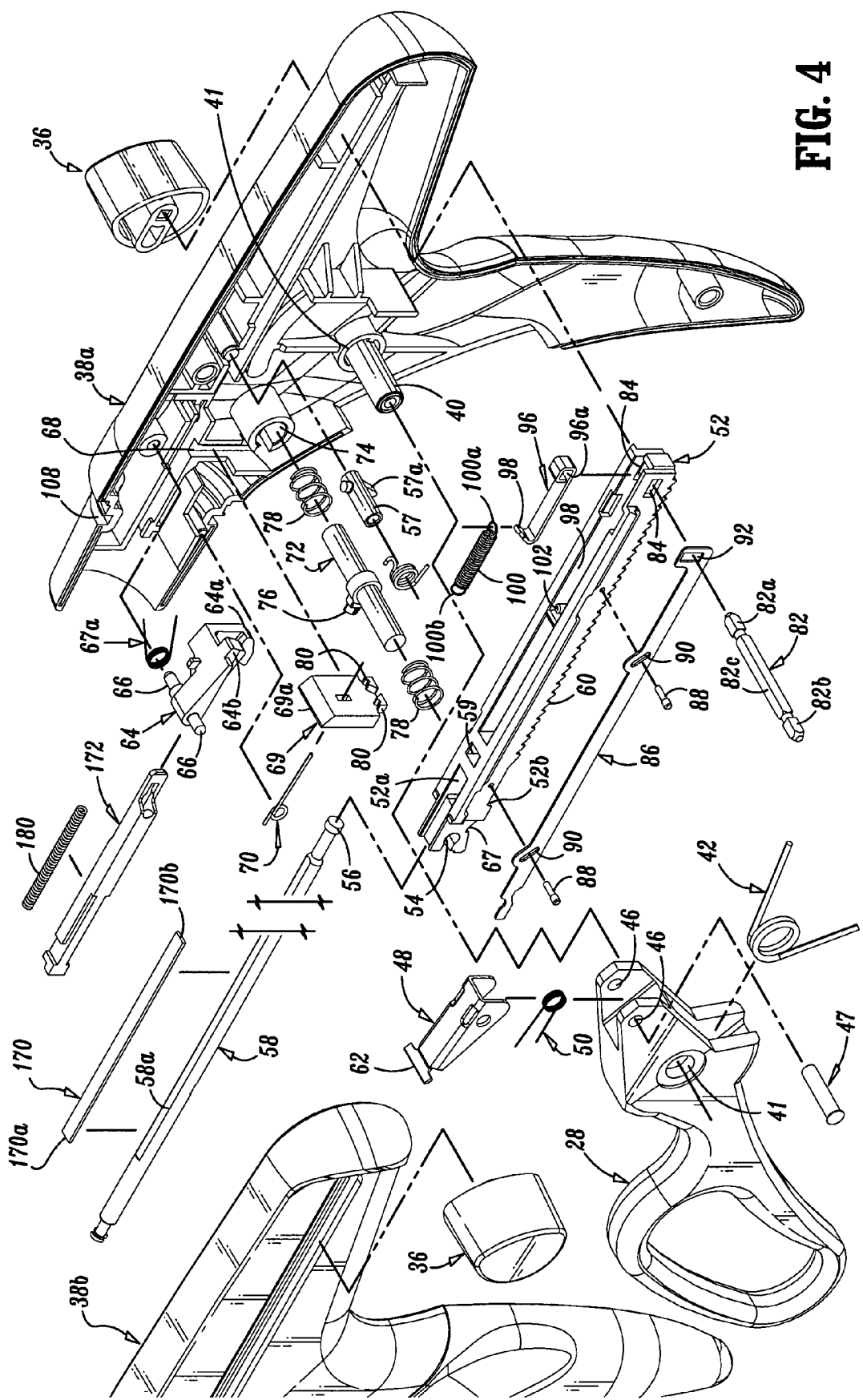
FIG. 4 is a partial exploded view of the handle assembly for the surgical stapling device of FIGS. 1-3.

After firing and before removing a loading unit, a retraction mechanism is employed. The retraction mechanism includes return knobs 36 (FIG. 1) which are connected to the proximal end of actuation shaft 52 by a coupling rod 82 (FIG. 4). Coupling rod 82 has right and left engagement portions 82a and 82b which extend through elongated slots 83 (FIG. 1) formed in housing half-sections 38a and 38b and are configured to receive return knobs 36. A central portion 82c of coupling rod 82 is dimensioned to be slidably received within slots 84 formed in the proximal end of actuation shaft 52. A release plate 86 is supported on one side of actuation shaft 52 by a pair of pins 88 (FIG. 4). Pins 88 are positioned within angled cam slots 90 formed through release plate 86. Coupling rod 82 extends through an opening 92 formed in the proximal end of release plate 86.

In use, when knobs 36 are pulled rearwardly by a surgeon, coupling rod 82 initially moves release plate 86 rearwardly in relation to actuation shaft 52 as rod 82 slides in slots 84 of actuation shaft 52. As this occurs, pins 88 cam release plate 86 downwardly to a position covering toothed rack 60 of actuation shaft 52 to disengage finger 62 of pawl 48 from toothed rack 60. When coupling rod 82 is pulled rearwardly to a position at which it engages the back end 84a of slots 84, additional rearward movement of knobs 36 effect proximal movement of actuation shaft 52 and firing rod 58.

A hook 96 is supported in a slot 98 formed in a top surface of actuation shaft 52. Hook 96 includes a throughbore 96a dimensioned to receive coupling rod 82. A forward end of hook 96 includes an upturned portion 98 configured to receive one looped end 100a of spring 100. The opposite end of spring 100 includes a loop 100b dimensioned to receive a post 102 formed on actuation shaft 52. Spring 100 is maintained in tension to urge coupling rod 82 towards the forward end of slots 84 in actuation shaft 52. When coupling rod 82 is positioned at the forward end of slots 84 of actuation shaft 52, release plate 86 is held or cammed in a raised position above toothed rack 60 of actuation shaft 52.

It will be understood that various modifications may be made to the embodiments disclosed herein. For example, the above described lock assembly may be incorporated into a variety of surgical instruments which include loading unit's and is not limited to use on endoscopic staplers. Further, the loading unit may be configured to receive an insertion tip of a surgical instrument in contrast to that disclosed. Therefore, the above description should not be construed as limiting, but merely as exemplifications of various embodiments. Those skilled in the art will envision other modifications within the scope and spirit of the claims appended hereto.

What is claimed is:

1. A surgical instrument comprising:
    an elongated body having a proximal end, a distal end, and a rod extending therethrough;
    a loading unit removably mountable on the elongated body and having a tool assembly;
    a sensor mechanism arranged for engagement by the loading unit and movement with the loading unit upon mounting of the loading unit on the elongated body, the sensor mechanism having a sensor tube configured to rotate along with the loading unit when the loading unit is mounted on the elongated body; and a handle assembly including a locking structure having a release flange, the locking structure having a first position for blocking movement of the sensor mechanism and a second position for allowing movement of the sensor mechanism so that the loading unit is removable from the elongated body when the sensor mechanism is in the second position, wherein the locking structure is configured to inhibit rotation of the sensor tube when located in the first position and the release flange rotates relative to the handle assembly and remains axially stationary with respect to the elongated body in response to translation of the locking structure between the first and second positions.

2. The surgical instrument according to claim 1, wherein the locking structure engages the rod when the locking structure is in the second position.

3. The surgical instrument according to claim 2, wherein the locking structure has a plunger arranged to engage the rod.

4. The surgical instrument according to claim 3, wherein the rod has a notch arranged for engagement by the plunger.

5. The surgical instrument according to claim 1, wherein the locking structure includes a button that is accessible by the user of the surgical instrument.

6. The surgical instrument according to claim 1, wherein the sensor tube is at least partially located within the elongated body.

7. The surgical instrument according to claim 1, wherein the sensor tube is attached to a movable yoke at a distal end of the sensor tube, the movable yoke being arranged for engagement with the loading unit.

8. The surgical instrument according to claim 1, wherein the sensor tube is attached to the release flange at a proximal end thereof.

9. The surgical instrument according to claim 8, wherein the locking structure includes a tang for blocking movement of the release flange when the locking structure is in the first position.

10. The surgical instrument according to claim 8, wherein the release flange includes a cam surface for camming a plunger into engagement with the rod.

11. The surgical instrument according to claim 1, wherein translation of the locking structure from the first position to the second position rotates the release flange.

12. The surgical instrument according to claim 11, wherein the release flange remains axially stationary during rotation.

13. The surgical instrument according to claim 1, wherein the release flange rotates relative to the elongated body.

14. A surgical instrument comprising:
an elongated body having a proximal end, a distal end, and a rod extending therethrough;
a loading unit removably mountable on the elongated body and having a tool assembly;
a sensor mechanism arranged for engagement by the loading unit, the sensor mechanism having a sensor tube that rotates with the loading unit coaxially with a longitudinal axis of the elongated body relative to the elongated body in order to releasably lock the loading unit on the elongated body in response to mounting the loading unit thereon; and
a handle assembly including a locking structure having a first position for blocking movement of the sensor mechanism and a second position for allowing movement of the sensor mechanism so that the loading unit is removable from the elongated body when the sensor mechanism is in the second position, wherein the locking structure is configured to inhibit rotation of the sensor tube when in the first position.

15. The surgical instrument according to claim 14, wherein the loading unit locks as the loading unit rotates into engagement with the elongated body.

16. The surgical instrument according to claim 14, wherein the sensor tube rotates relative to the handle assembly.

* * * * *